US012605491B2

(12) United States Patent
Tekin et al.

(10) Patent No.: US 12,605,491 B2
(45) Date of Patent: Apr. 21, 2026

(54) BREASTMILK COLLECTION

(71) Applicant: Lansinoh Laboratories, Inc.,
Alexandria, VA (US)

(72) Inventors: Selim Tekin, Izmir (AR); Ersoy Onur Solakoğlu, Izmir (AR)

(73) Assignee: Lansinoh Laboratories, Inc.,
Alexandria, VA (US)

( * ) Notice: Subject to any disclaimer, the term of this patent is extended or adjusted under 35 U.S.C. 154(b) by 0 days.

(21) Appl. No.: 19/289,631

(22) Filed: Aug. 4, 2025

(65) Prior Publication Data

US 2026/0034280 A1  Feb. 5, 2026

Related U.S. Application Data

(60) Provisional application No. 63/679,306, filed on Aug. 5, 2024.

(51) Int. Cl.
| | |
|---|---|
| *A61M 1/06* | (2006.01) |
| *A61M 1/00* | (2006.01) |
| *A61M 39/24* | (2006.01) |

(52) U.S. Cl.
CPC .............. *A61M 1/067* (2021.05); *A61M 1/60* (2021.05); *A61M 39/24* (2013.01)

(58) Field of Classification Search
CPC ........ A61M 1/06; A61M 1/064; A61M 1/066; A61M 1/067; A61M 1/069
See application file for complete search history.

(56) References Cited

U.S. PATENT DOCUMENTS

| | | | |
|---|---|---|---|
| 8,057,425 | B1 | 11/2011 | Myers et al. |
| 8,187,227 | B2 | 5/2012 | Luzbetak et al. |
| 10,434,230 | B2 * | 10/2019 | Rigert .................... A61M 1/06 |
| 10,926,011 | B2 | 2/2021 | O'Toole et al. |
| 11,554,198 | B1 * | 1/2023 | Pan ........................ A61M 1/062 |
| 12,016,985 | B2 | 6/2024 | Visconti et al. |
| 2002/0193731 | A1 | 12/2002 | Myers et al. |
| 2004/0087898 | A1 | 5/2004 | Weniger |
| 2008/0171970 | A1 | 7/2008 | Luzbetak et al. |
| 2013/0023821 | A1 | 1/2013 | Khalil et al. |
| 2014/0364035 | A1 | 12/2014 | Abbaszadeh |
| 2015/0217033 | A1 | 8/2015 | Pollen et al. |
| 2015/0217037 | A1 * | 8/2015 | Pollen .................... A61M 1/78 604/74 |
| 2015/0328380 | A1 | 11/2015 | Furrer et al. |
| 2015/0335800 | A1 | 11/2015 | Yamashita |
| 2016/0058928 | A1 | 3/2016 | Nowroozi et al. |
| 2018/0021491 | A1 * | 1/2018 | Rigert .................... A61M 1/06 604/74 |

(Continued)

FOREIGN PATENT DOCUMENTS

| | | | |
|---|---|---|---|
| EP | 3 058 967 | A1 | 8/2016 |
| WO | 2008057218 | A2 | 5/2008 |
| WO | 2019/194418 | A1 | 10/2019 |

*Primary Examiner* — David P. Olynick

(74) *Attorney, Agent, or Firm* — Merchant & Gould P.C.

(57) ABSTRACT

A wearable breastmilk collection device can include: a collection receptacle; a flange chamber, wherein the flange chamber and collection receptacle comprise a hinge assembly configured to pivot the flange chamber and collection receptacle to a closed position; at least one snap configured to secure the flange chamber and collection receptacle together in the closed position; and a diaphragm disposed between the flange chamber and the collection receptacle.

13 Claims, 29 Drawing Sheets

(56) References Cited

U.S. PATENT DOCUMENTS

| | | | |
|---|---|---|---|
| 2018/0104396 A1 | 4/2018 | Park | |
| 2018/0361040 A1 | 12/2018 | O'Toole et al. | |
| 2022/0401639 A1 | 12/2022 | O'Toole et al. | |
| 2023/0111110 A1 | 4/2023 | De Becdelievre et al. | |
| 2024/0001010 A1* | 1/2024 | Chen | A61M 1/066 |
| 2024/0238488 A1* | 7/2024 | Xiao | A61M 1/064 |
| 2025/0073380 A1* | 3/2025 | Zheng | A61M 1/064 |
| 2025/0114501 A1* | 4/2025 | Chen | A61M 1/06 |

* cited by examiner

1100

Bottle

Manifold

Diaphragm

Cap

Bottle
(locking ring and cap remain in place during cleaning)

Diaphragm

Flange

BREASTMILK COLLECTION

RELATED APPLICATION(S)

This application is related to U.S. patent application Ser. No. 17/450,647 filed on Oct. 12, 2021, which is hereby incorporated by reference in its entirety.

BACKGROUND

Breastmilk contains all the nutrients a baby needs for the first six months of life to support growth and development. Therefore, breastfeeding and/or breastmilk feeding is recommended globally by the World Health Organization and healthcare professionals. When possible, mothers should be supported to initiate breastfeeding within the first hour of their baby's life, breastfeed exclusively for six months, and continue breastfeeding while giving appropriate complementary foods for up to two years of age or beyond. There are situations, however, when direct breastfeeding is not possible. For example, babies may not be able to latch and suckle, due to cleft palate or tongue tie, prematurity, low birthweight, or other causes, and mothers may not be able to breastfeed due to medical conditions or recovery from birth trauma. In such cases, human breastmilk feeding becomes the next best option. The principle methods used by mothers to collect human breastmilk are hand expressing breastmilk into a container and expressing breastmilk using a manual or electric breast pump. For many mothers, a breast pump plays a significant role in the breastmilk feeding process. Unfortunately, breast pumps are often cumbersome, obtrusive, noisy and inconvenient to carry from place to place and use.

Discretion and mobility are poorly met needs. Traditional breast pump systems use collection kits that include breast flanges and bottles. Although effective, these systems do not support discretion, mobility or ease of use and assembly. More recent systems use pump systems and/or collection cups that fit inside a breast pumping mother's bra but include at least five components, not including tubing or a suction source. These systems tend to be difficult to use and complicated to assemble. Therefore, there is a distinct need for a breastmilk expression system that is more convenient, comfortable and unobtrusive. Ideally, such a system would facilitate emptying as much breastmilk as possible from a breast, to increase milk supply and minimize risk of breast engorgement. Also ideally, the system would be relatively easy to use, require only minimal/simple assembly, would enable a woman to express milk discretely, and would provide for easier mobility.

SUMMARY OF THE INVENTION

Regularly expressing breastmilk, whether by nursing or pumping, is a critical factor for mothers to establish and maintain breastmilk supply, even if an infant is not nursing at all or not nursing well. This disclosure describes a device and system that offers flexibility and convenience for pumping and collecting expressed breastmilk. In most embodiments, the device fits in a brassiere and is attached to an electric pump using silicone tubes for applying vacuum to the device's pump. In other embodiments, the pump is directly attached to the device. The breastmilk collection device, securely supported by a brassiere, becomes a hands-free device that enables the lactating mother to pump and/or collect expressed milk without holding the device. It also allows a woman to pump and collect expressed breastmilk from one breast while breastfeeding an infant on the other breast.

According to various embodiments, the breastmilk collection system described herein can include: a collection receptacle; a flange chamber, wherein the flange chamber and collection receptacle comprise a hinge assembly configured to pivot the flange chamber and collection receptacle to a closed position; at least one snap configured to secure the flange chamber and collection receptacle together in the closed position; and a diaphragm disposed between the flange chamber and the collection receptacle.

DETAILED DESCRIPTION

Figures 1A, 1B:
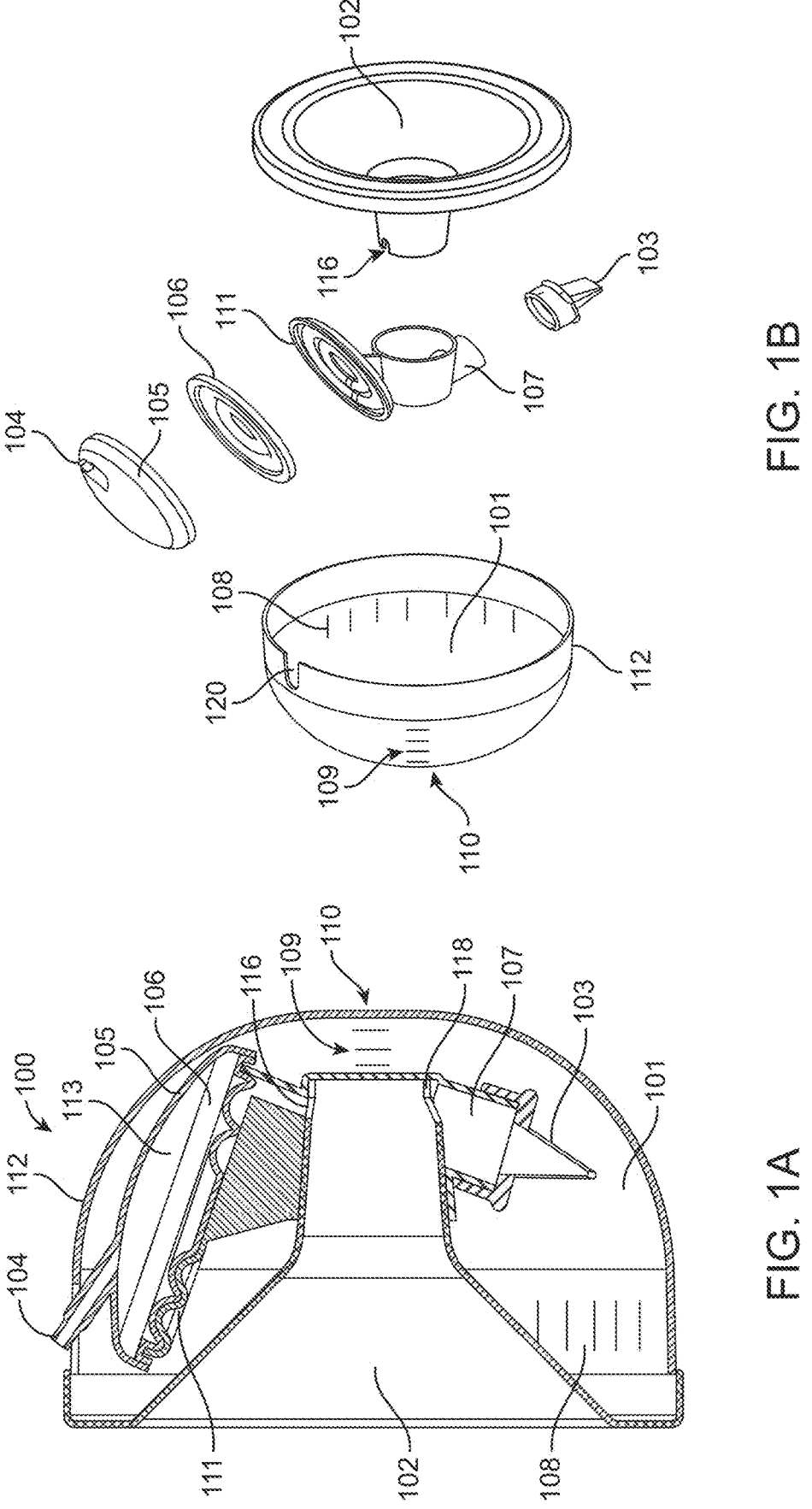
FIG. 1A is a side, cross-sectional view of a breastmilk collection device, according to one embodiment.
FIG. 1B is an exploded view of the breastmilk collection device of FIG. 1A.

FIGS. 1A and 1B illustrate one embodiment of a wearable breastmilk collection cup (100) for collection of breastmilk while being positioned in the woman's brassier. The wearable collection cup (100) contains a storage compartment (101) created by the coupling of the breast accepting flange (102) and the cup (112) and is separated from a breast accepting flange (102) by a one-way valve (103) such as but not limited to a duckbill valve. The collection cup (100) is operated under variable suction parameters of vacuum through an external vacuum source attachment (104) that provides suction to an isolated reservoir (113) comprising a half dome (105). The isolated half dome is created by compressing the half dome top (105) against the flexible diaphragm (106) and a flange receiver (111) comprising a lower vacuum communication wall with outlet to the breast accepting flange chamber (102). Communication of the suction force from the isolated reservoir (113) to the breast accepting flange compartment (102) is done through a flexible separating diaphragm (106). Vacuum force is actuated from the flexible separating diaphragm (106) in cycles which help to extract milk or colostrum from the breast and allow it to flow into a collection compartment (107) anterior to the one-way valve (103). The wearable collection cup (100) also may include either or both horizontal (108) or vertical (109) measurement lines to help the user determine the volume of fluid contained within the wearable collection cup (100) if the cup (112) was in place on the breast vertically or placed on the table in the prone position with the flat resting edge (110) touching the table.

Figures 2A, 2B:
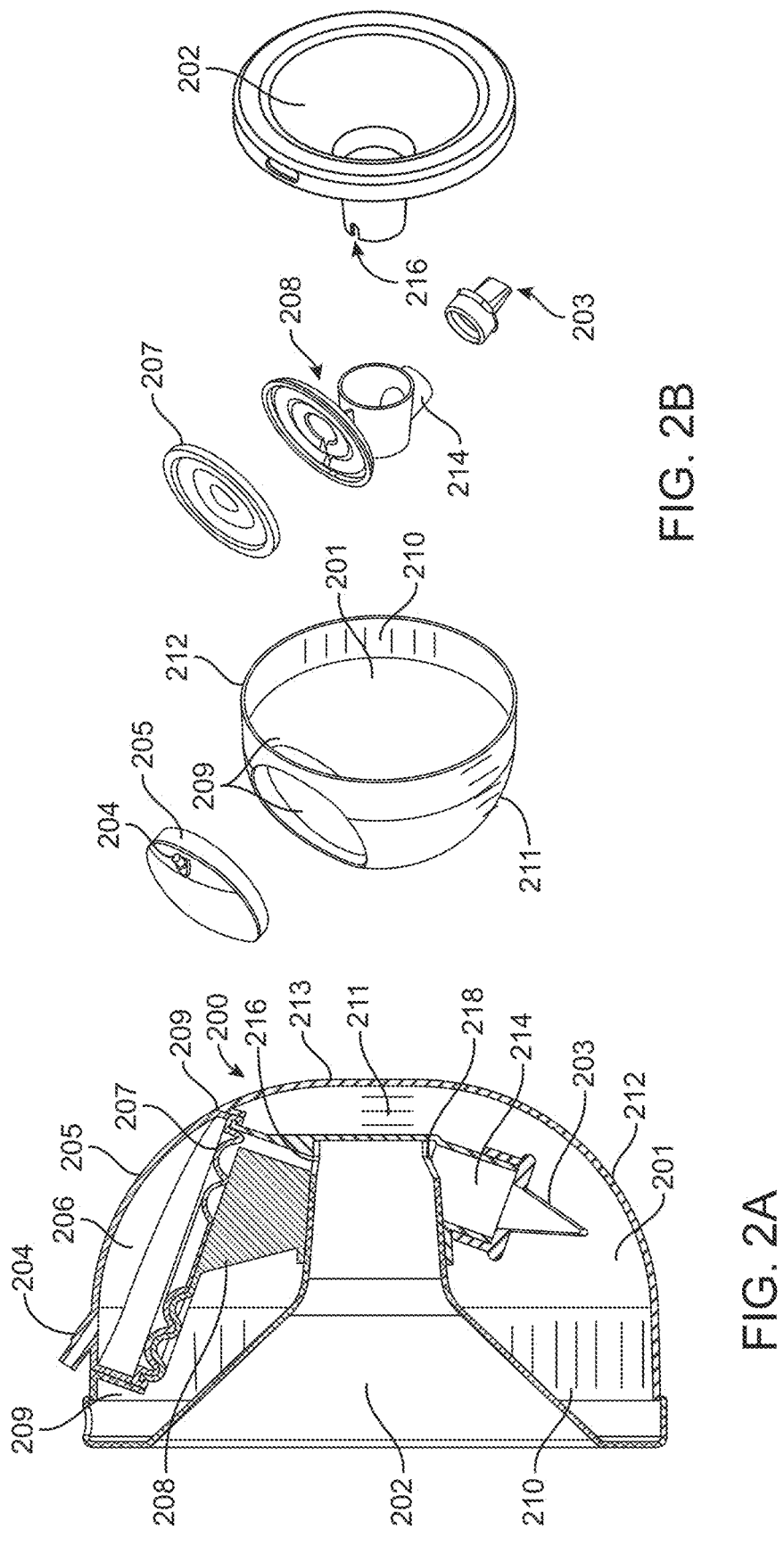
FIG. 2A is a side, cross-sectional view of a breastmilk collection device, according to an alternative embodiment.
FIG. 2B is an exploded view of the breastmilk collection device of FIG. 2A.

FIGS. 2A and 2B illustrate an alternative embodiment of a wearable breastmilk collection cup (200). The wearable breastmilk collection cup (200) contains a storage compartment (201) created by the coupling of the breast accepting flange (202). The cup (212) is separated from a breast accepting flange (202) by a one-way valve (203), such as but not limited to a duckbill valve. The collection cup (200) is operated under variable suction parameters of vacuum through an external vacuum source attachment (204) that is on top of a half dome (205) to provide suction to an isolated reservoir (206). The isolated reservoir (206) created by compressing the half dome (205) against the flexible diaphragm (207) is securely locked by a receptacle (209) of the cup (212) and creates complete seal to store expressed breastmilk. The isolated half dome (205) and a flange receiver (208) comprising a lower vacuum communication wall with outlet to the breast accepting flange compartment (202). Communication of the suction force from the isolated reservoir (206) to the breast accepting flange compartment (202) is done through a flexible separating diaphragm (207). Vacuum force is actuated from the flexible separating diaphragm (207) in cycles which help to extract milk or colostrum from the breast and allow it to flow into a collection compartment (214) anterior to the one-way valve (203). The wearable collection cup (200) also may or may not include either or both horizontal (210) or vertical (211) measurement lines all the way from bottom to up to be used by the user to determine the volume of fluid contained within the wearable collection cup (200) if the cup (212) was in place on the breast vertically or placed on the table in the prone position with the flat resting edge (213) touching the table.

Figure 3B:
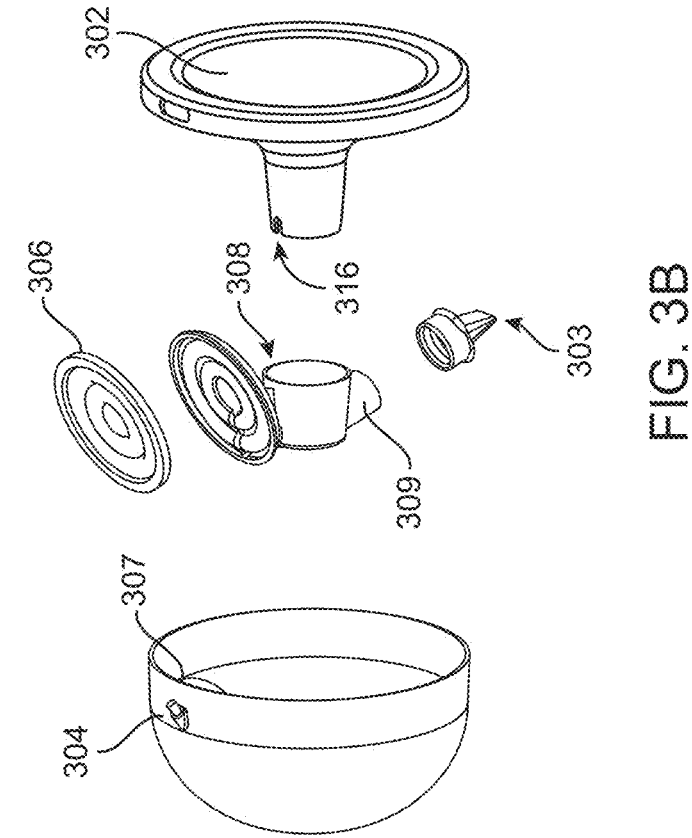
FIG. 3B is an exploded view of the breastmilk collection device of FIG. 3A.
Figure 3A:
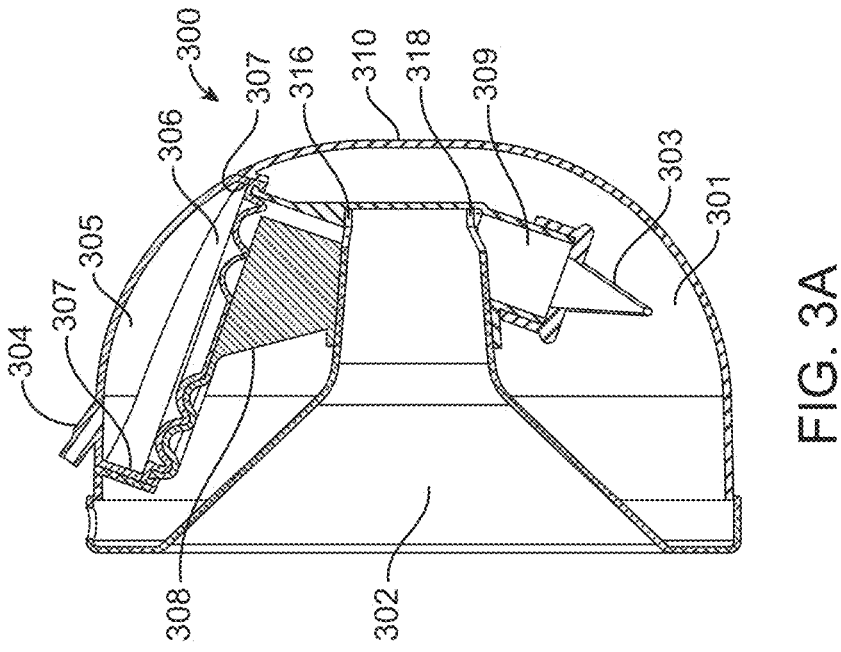
FIG. 3A is a side, cross-sectional view of a breastmilk collection device, according to an alternative embodiment.

FIGS. 3A and 3B illustrate another alternative embodiment of a wearable breastmilk collection cup (300). The wearable collection cup (300) contains a storage compartment (301) created by the coupling of the breast accepting flange (302) and the cup (310) and is separated from a breast accepting flange (302) by a one-way valve (303), such as but not limited to a duckbill valve. The collection cup (300) is operated under variable suction parameters of vacuum through an external vacuum source attachment (304) on the cup (310) that provides suction to an isolated reservoir (305). The isolated reservoir (305) is created by the cup (310) against the flexible diaphragm (306) and securely locking the flexible diaphragm (306) by a receptacle (307) that allows the collection cup (300) to eliminate one of the components. A flange receiver (308) comprising a lower vacuum communication wall with outlet to the breast accepting flange chamber (302). Communication of the suction force from the isolated reservoir (305) to the breast accepting flange compartment (302) is done through a flexible separating diaphragm (306). Vacuum force is actuated from the flexible separating diaphragm (306) in cycles which help to extract milk or colostrum from the breast and allow it to flow into a collection compartment (309) anterior to the one-way valve (303).

Figure 4B:
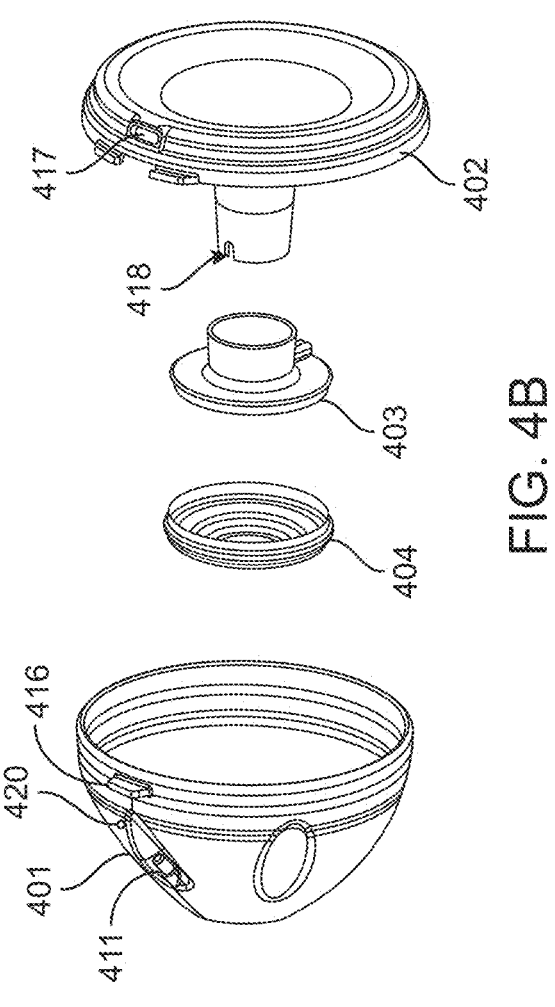
FIG. 4B is an exploded view of the breastmilk collection device of FIG. 4A.
Figure 4A:
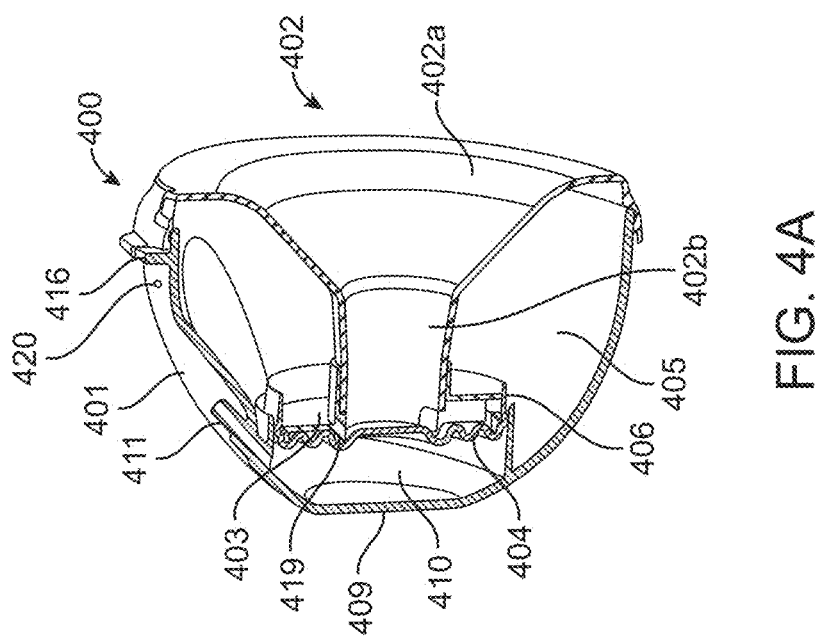
FIG. 4A is a side, cross-sectional view of a breastmilk collection device, according to an alternative embodiment.

FIGS. 4A and 4B illustrate another alternative embodiment of a wearable collection cup (400). The wearable collection cup (400) includes a collection receptacle (401), breast accepting flange chamber (402), flange receiver (403) and diaphragm/one-way valve (404). The system contains a storage compartment (405) that receives the expressed breastmilk and is contained within the collection receptacle (401) breast accepting flange chamber (402) and diaphragm/one-way valve (404). The storage compartment (405) is created by the coupling of the breast accepting flange compartment (402) and the collection receptacle (401) and is separated from a breast accepting flange chamber (402) by the diaphragm/one-way valve one-way valve (404)

Figure 4C:
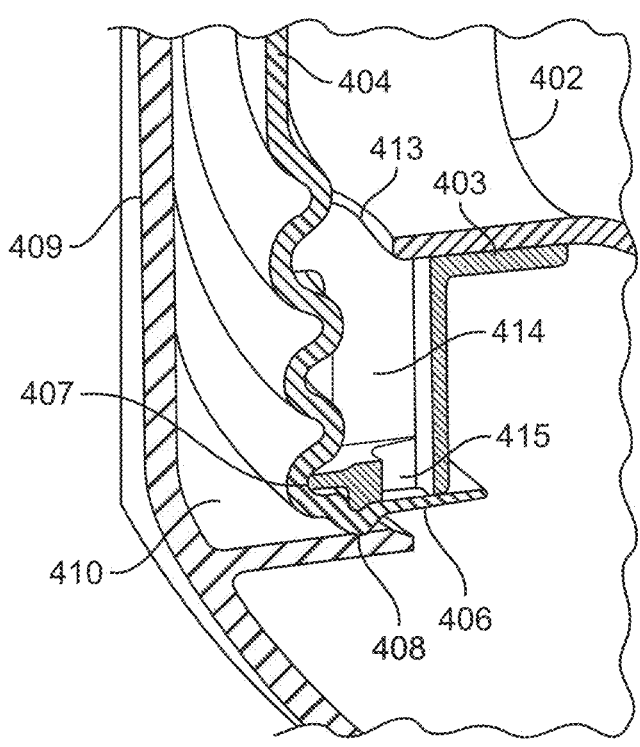
FIGS. 4C and 4D are partial cross-sectional views of the breastmilk collection device of FIGS. 4A and 4B, illustrating a path for milk flow through the device.
Figure 4D:
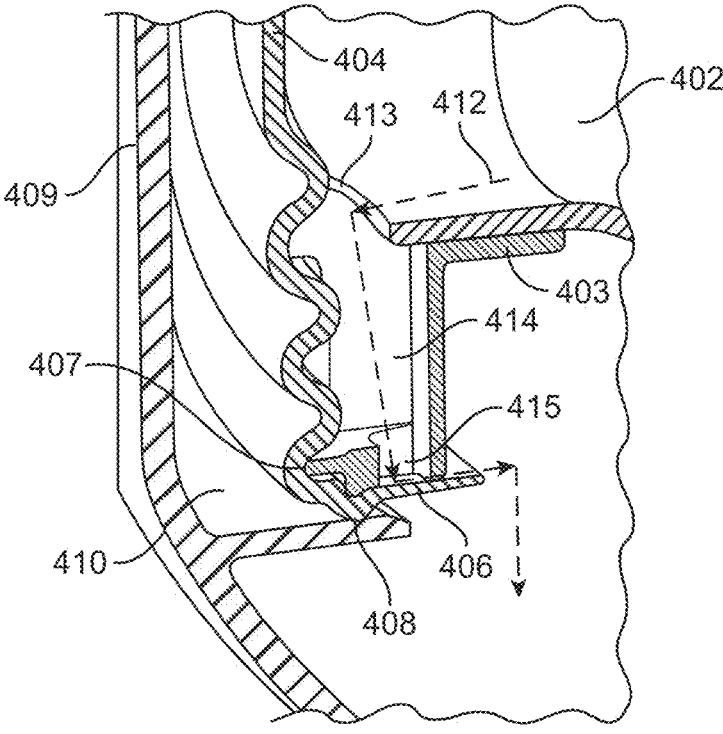

Referring to FIGS. 4C and 4D, the diaphragm/one-way valve (404) includes an integrated one-way valve (406) shown as but not limited to a flapper valve and is in direct contact with the flange receiver (403) and collection receptacle (401). Said contact creates both an inner seal (407) and outer seal (408). The diaphragm/one-way valve (404) is captured between the flange receiver (403) and the collection receptacle (401) whose half dome top (409) forms an isolated reservoir (410) with the diaphragm/one-way valve (404). The isolated reservoir (410) is created by compressing the flange receiver (403) against the flexible diaphragm/one-way valve (404) and collection receptacle (401).

The wearable collection cup (400) is operated under variable suction parameters of vacuum through an external vacuum source attachment (411) that provides suction to an isolated reservoir (410). Communication of the suction force from the isolated reservoir (410) to the breast accepting flange compartment (402) is done through a flexible separating diaphragm/one-way valve (404). Vacuum force is actuated from the flexible separating diaphragm (404) in cycles which help to extract milk or colostrum from the breast and allow it to flow into the storage compartment (405) anterior to the one-way valve (406). The flow path (412) from the breast accepting flange chamber (402) to the collection receptacle (401) includes the flow entrance (413), located at the distal end of the breast accepting flange chamber (402), flow chamber (414) and flow exit (415). As air is pushed back into isolated reservoir (410) and milk flows into the storage compartment (405) there is an amount of air that is displaced and exits through a vent hole (418) which may or may not comprise a float restrictor or valve to prevent spillage through the vent hole (418) when a user bends over. Some systems may not need a vent hole (418) if the requisite amount of air displaced vents around another part of the seal mechanism above the liquid level.

To ensure proper flow an alignment mechanism is needed which aligns the breast accepting flange chamber (402), the collection receptacle (401) and the flange receiver (403). During assembly the flange receiver (403) is pressed onto the breast accepting flange compartment (402) and the internal post (418) accepts the internal post (419). Then the external post (416) is placed into the external key way (417) prior to pressing the breast accepting flange compartment (402) onto the collection receptacle (401)

FIGS. 5A-5D illustrate another alternative embodiment of a wearable collection cup (500). The wearable collection cup (500) contains an external breast pump (501) that is attachable to a collection receptacle (502). The collection cup (500) is operated under variable suction parameters of vacuum by the external breast pump (501) and is connected to an external vacuum source attachment (504) by the pump connecter (505). Using the pump connector (504) gives a pumping mother the option of using different external breast pumps.

Figure 5A:
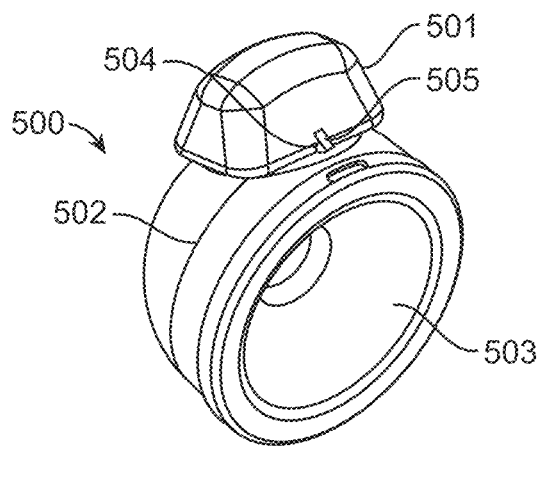
FIGS. 5A-5C are perspective, side and front views, respectively, of a breastmilk collection device with an electric pump, according to one embodiment.
Figure 5B:
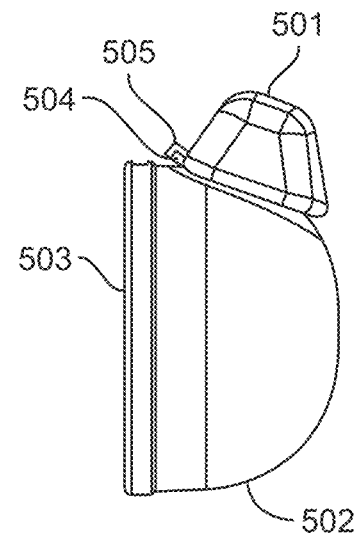
Figure 5C:
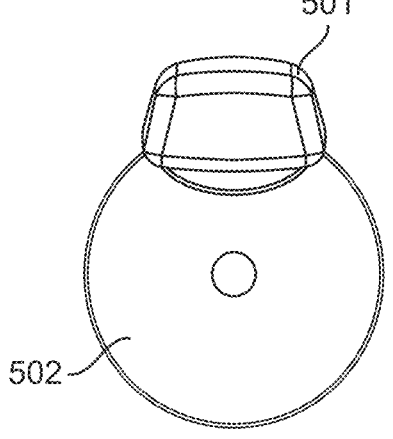
Figure 5D:
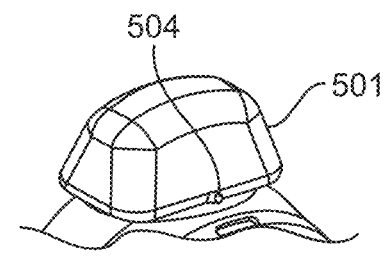
FIG. 5D is a partial perspective view of the breastmilk device of FIGS. 5A-5C, illustrating an optional light for nighttime visualization.
Figures 5E, 5F, 5G:
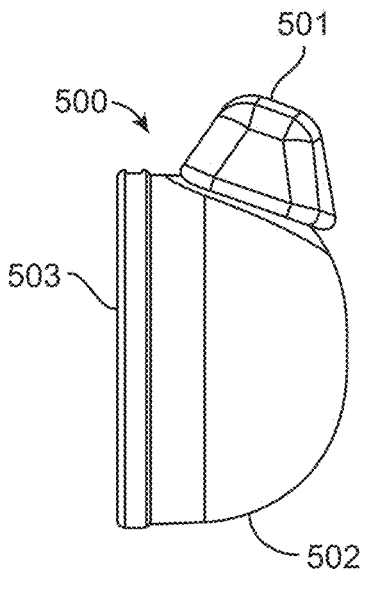
FIGS. 5E-5G are side, partial cross-section and exploded views, respectively, of the breastmilk collection device of FIGS. 5A-5D.

FIGS. 5E-5G illustrate a wearable collection cup (500) where the wearable collection cup (500) contains an external breast pump (501) that is attachable to a collection receptacle (502). In this instance the pump is connected directly to the isolated reservoir (511) by the vacuum communication conduit (506). The collection cup (500) is operated under variable suction parameters of vacuum by the external breast pump (501) and is connected to vacuum communication conduit (506) such that it provides suction to an isolated reservoir (511). The isolated reservoir (511) is created by pressing the external breast pump (501) into the pump connection cylinder and compressing the flexible diaphragm/one-way valve (509) to the half dome top (510).

Figure 5H:
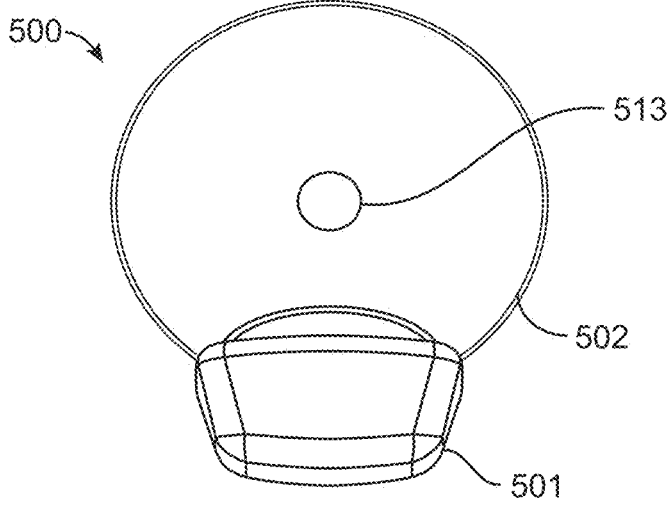
FIGS. 5H and 5J are top views of the breastmilk collection device of FIGS. 5A-5G, illustrating operation of the optional light.

FIG. 5H illustrates a wearable collection cup (500) where the wearable collection cup (500) contains an external breast pump (501) that is located below the targeted nipple location (513) enabling visualization, supporting consistent nipple placement and overall proper use.

Figure 5J:
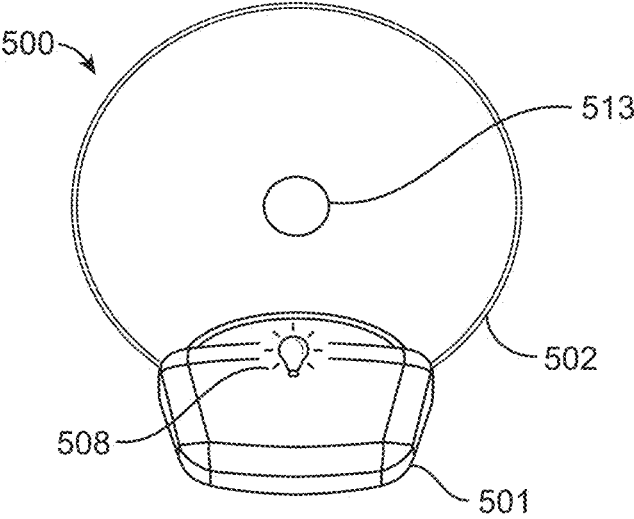

FIG. 5J illustrates a wearable collection cup (500) where the wearable collection cup (500) contains an external breast pump (501) that is located below the targeted nipple location (513) and a light (508) that can be switched on and off enabling better visualization and supporting consistent nipple placement and overall proper use.

Figures 5K, 5L, 5M, 5N:
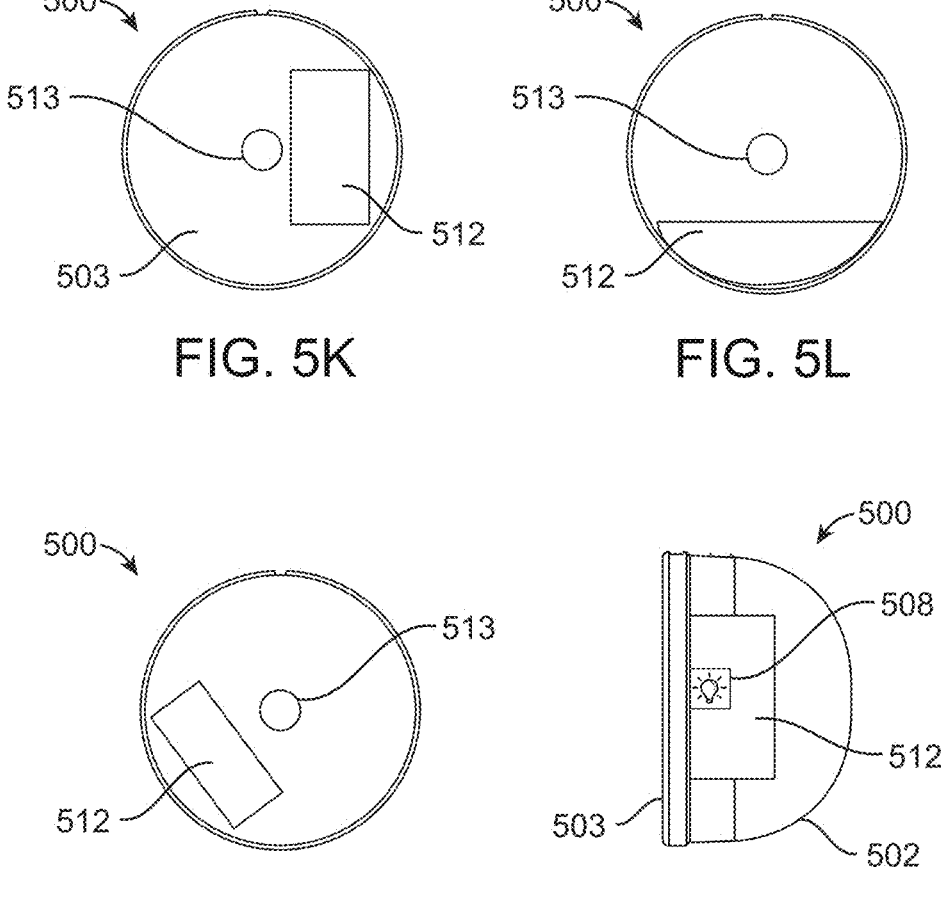
FIGS. 5K-5N are additional views of the breastmilk collection device of FIGS. 5A-H and 5J.

FIGS. 5K-5M illustrate a wearable collection cup (500) for collection of breastmilk from a mother by being placed in her brassier such that when the device is in use the mother can be hands-free. The wearable collection cup (500) contains an internal breast pump (512) that is located within the collection receptacle (502), but not in direct communication or contact with the collected breastmilk. The internal breast pump (512) can be located in a plurality of positions while still enabling better visualization and supporting consistent nipple placement and overall proper use.

FIG. 5N describes a wearable collection cup (500) where the wearable collection cup (500) contains an internal breast pump (512) such that a breast pump is an electromechanical device that generates a oscillating suction wave that is located below the targeted nipple location (513) and a light (508) that can be switched on and off enabling better visualization and supporting consistent nipple placement and overall proper use.

FIGS. 6A-6D illustrate another embodiment of a breastmilk collection system (600). The breastmilk collection system (600) includes a collection receptacle (601), breast accepting flange chamber (602), flange receiver (603), diaphragm/one-way valve (604) and bottle flange (605). The system contains a storage compartment (606) that receives the expressed breastmilk and is contained within the collection receptacle (601) bottle flange (605) and diaphragm/one-way valve (604).

Figures 6A, 6B, 6C:
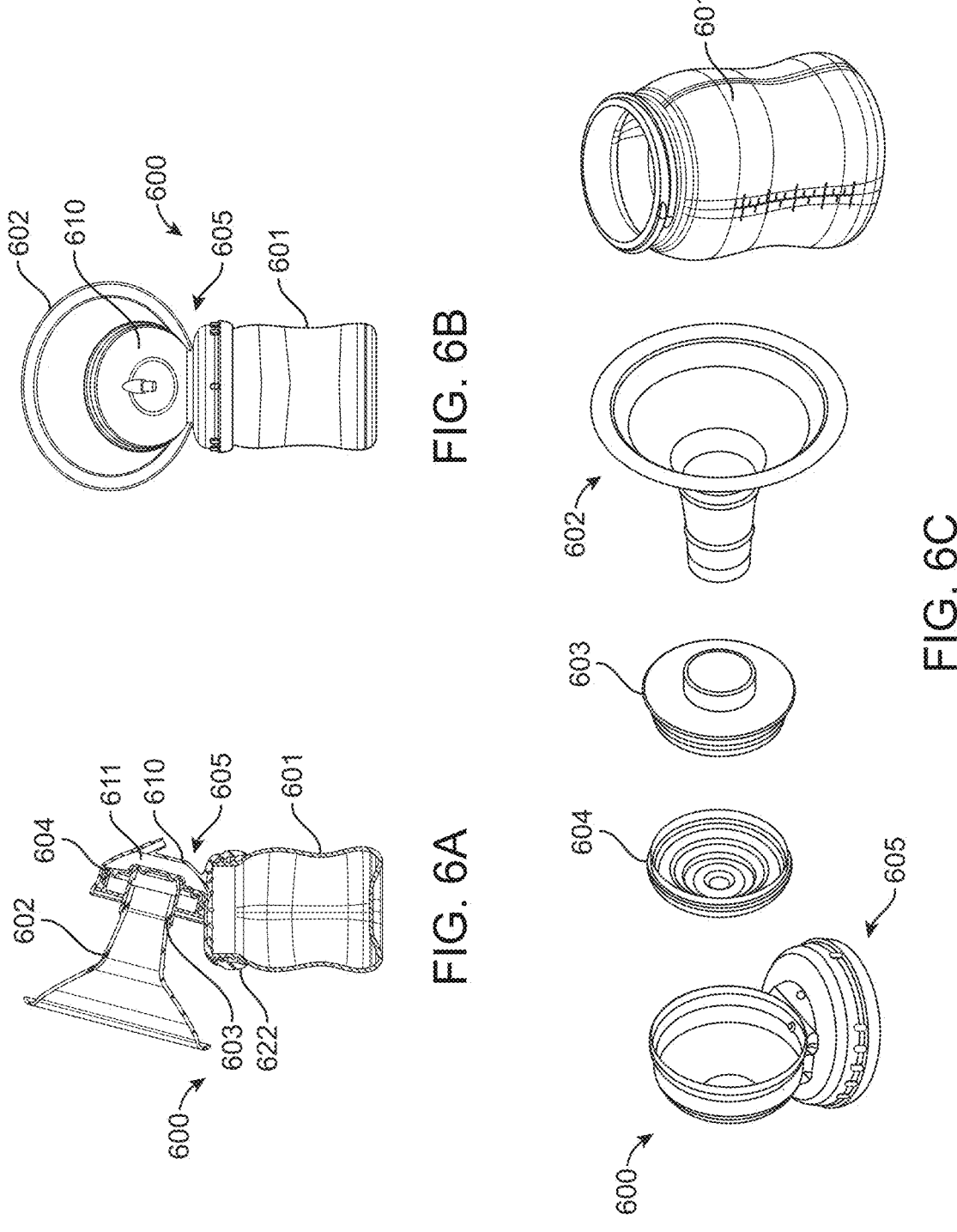
FIGS. 6A-6C are side/cross-sectional, rear and exploded views, respectively, of a breastmilk collection device according to another alternative embodiment.
Figure 6D:
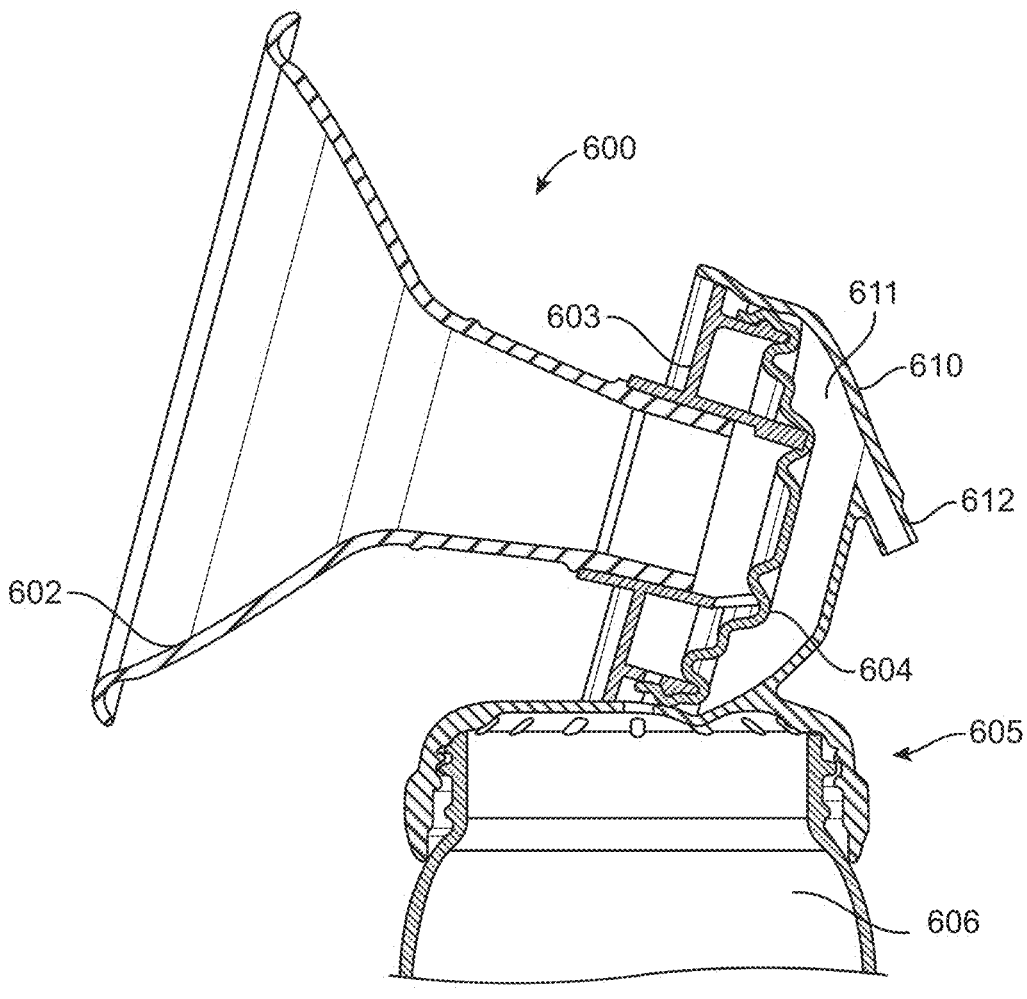
FIG. 6D is a close-up view of a portion of FIG. 6A.
Figure 6E:
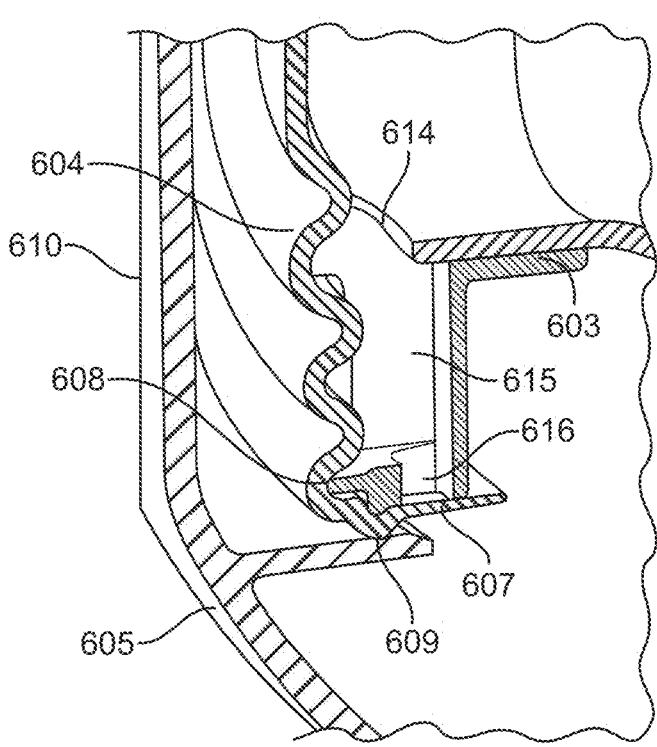
FIGS. 6E and 6F are close-up views of another portion of the breastmilk collection device of FIGS. 6A-6C.
Figure 6F:
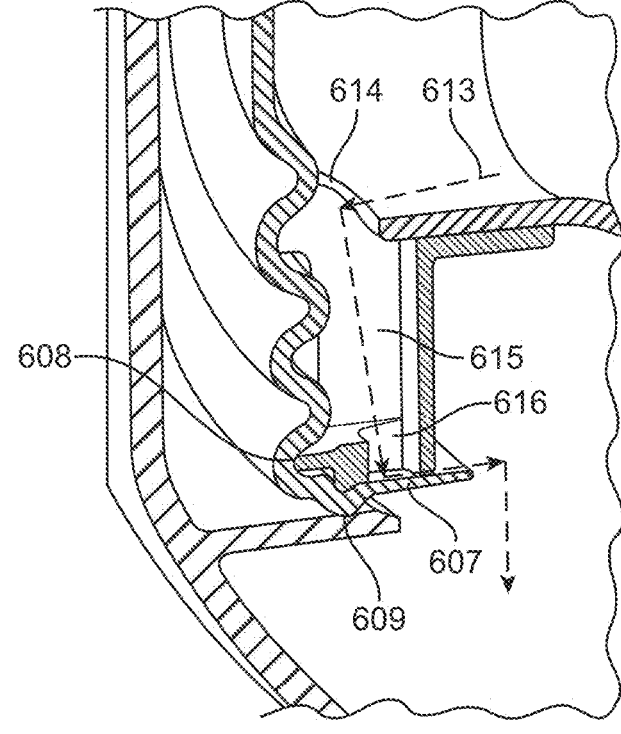

Referring to FIGS. 6E and 6F, the diaphragm/one-way valve (604) includes an integrated one-way valve (607) shown as but not limited to a flapper valve and is directly connected to the flange receiver (603) and bottle flange (605). Said connection creates both an inner seal (608) and outer seal (609). The diaphragm/one-way valve (604) is captured between the flange receiver (603) and the bottle flange (605) whose half dome top (610) forms an isolated reservoir (611) with the diaphragm/one-way valve (604). The isolated reservoir (611) is created by compressing the flange receiver (603) against the flexible diaphragm/one-way valve (604) and bottle flange (605).

The breastmilk collection system (600) is operated under variable suction parameters of vacuum through an external vacuum source attachment (612) that provides suction to an isolated reservoir (611). Communication of the suction force from the isolated reservoir (611) to the breast accepting flange compartment (602) is done through a flexible separating diaphragm/one-way valve (604). Vacuum force is actuated from the flexible separating diaphragm (604) in cycles which help to extract milk or colostrum from the breast and allow it to flow into the storage compartment (606) anterior to the one-way valve (607). The flow path (613) from the breast accepting flange chamber (602) to the collection receptacle (601) includes the flow entrance (614), located at the distal end of the breast accepting flange chamber (602), flow chamber (615) and flow exit (616).

Figures 6G, 6H:
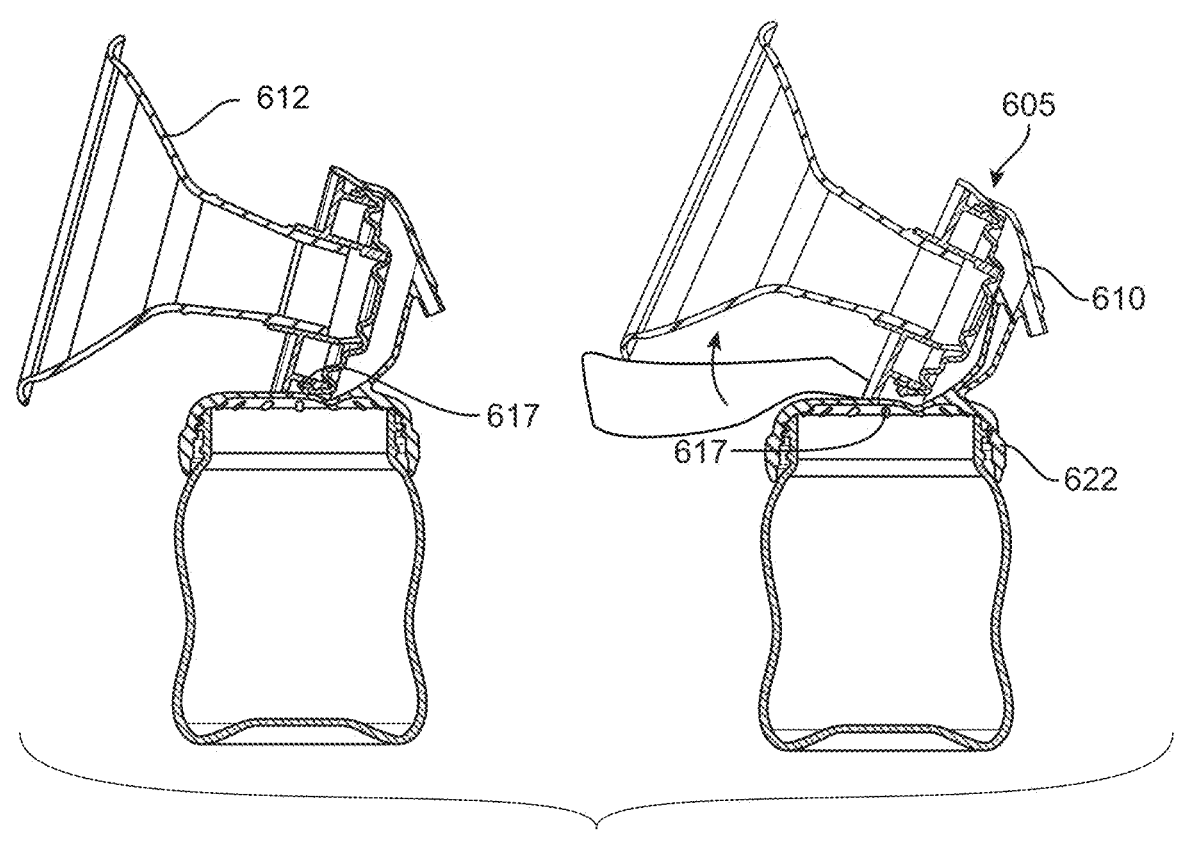
FIG. 6G is a side, cross-sectional view of the breastmilk collection device of FIGS. 6A-6C, illustrating adjustability.
FIG. 6H is two perspective views of a top portion of the breastmilk collection device of FIGS. 6A-6C.

FIG. 6G incorporates a tilting mechanism (617) that enables a change in breast accepting flange chamber (602) angle such that a more comfortable pumping position for mom can be established.

FIG. 6H incorporates a rotation mechanism (618) that enables a change in bottle flange (605) position such that a more comfortable pumping position for mom can be established. A bottle vent hole (619) on the cap of the bottle enables air displaced by the movement of milk or colostrum into the bottle to be vented.

Figures 7A, 7B, 7C, 7D, 7E, 7F:
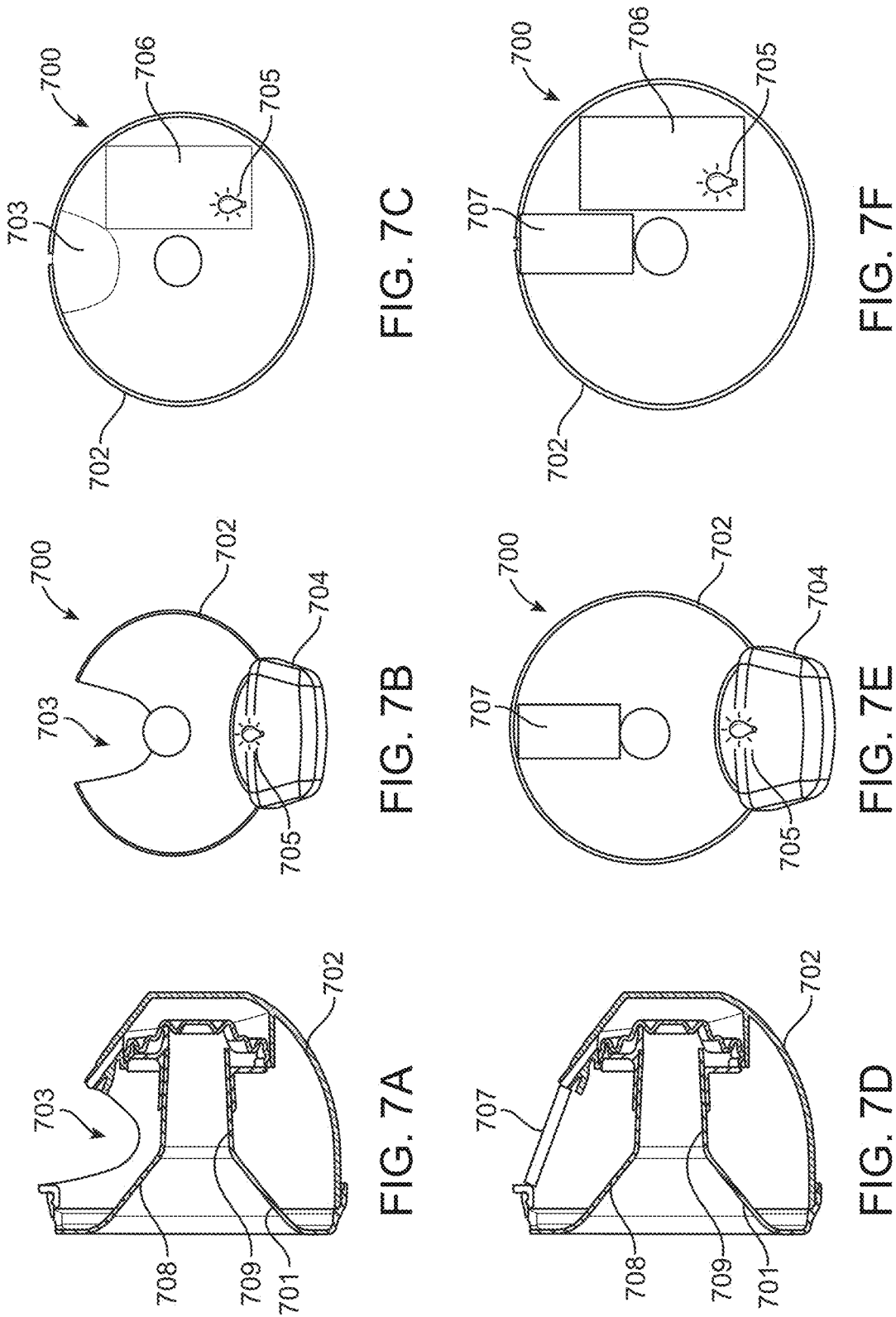
FIGS. 7A-7F are various views of a collection cup system for a breastmilk collection device, according to one embodiment.

FIGS. 7A-7C illustrate another alternative embodiment of a wearable collection cup (700) for collection of breastmilk from a mother. The wearable collection cup (700) contains either an external breast pump (704) that is attachable to a collection receptacle (702) or an internal breast pump. The collection receptacle (702) has a visualization recess (703) that comes in close proximity to the area where the entrance cone (708) intersects with the nipple accepting tunnel (709). The visualization recess (703) is located on the upper, outer portion of the collection receptacle (702) enabling better visualization and supporting consistent nipple placement and overall proper use.

FIGS. 7D-7F describe a wearable collection cup (700) for collection of breastmilk from a mother by being placed in her brassier such that when the device is in use the mother can be hands-free. The wearable collection cup (700) contains either an external breast pump (704) and light (705) that is attachable to a collection receptacle (702) or an internal breast pump (706) which the pump could comprise one or more of different drive mechanisms for creating vacuum including a voice coil actuator with accumulator valves, a rotary diaphragm motor, a piston pump, and or a piezo electric motor system, and light (705). The collection receptacle (702) has a visualization lens (707) located in the upper portion of the collection receptacle (702). The visualization lens could be molded into the collection receptacle or could be a separate component that is joined to the collection receptacle (702). The visualization lens (703) is located on the upper, outer portion of the collection receptacle (702) enabling better visualization and supporting consistent nipple placement and overall proper use.

Figure 8B:
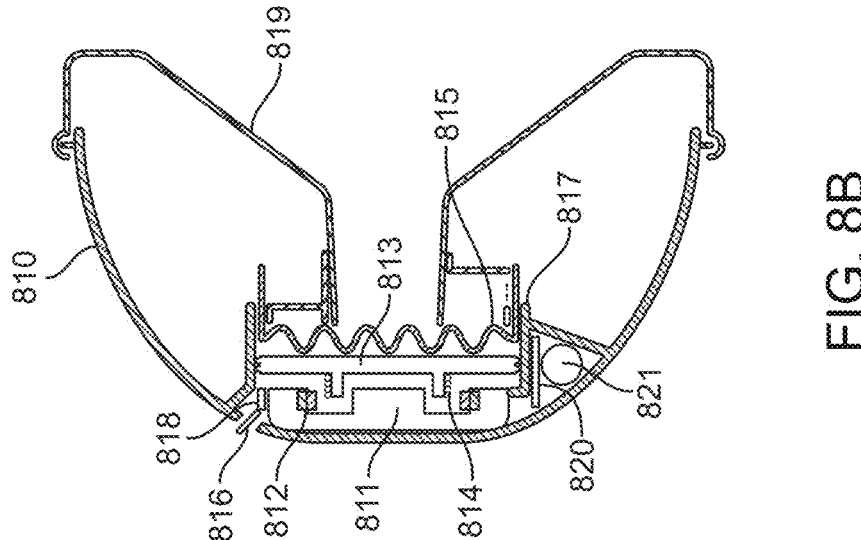
FIGS. 8A-8B are various wearable breast pump collections systems driven by electromechanical actuation of components.
Figure 8A:
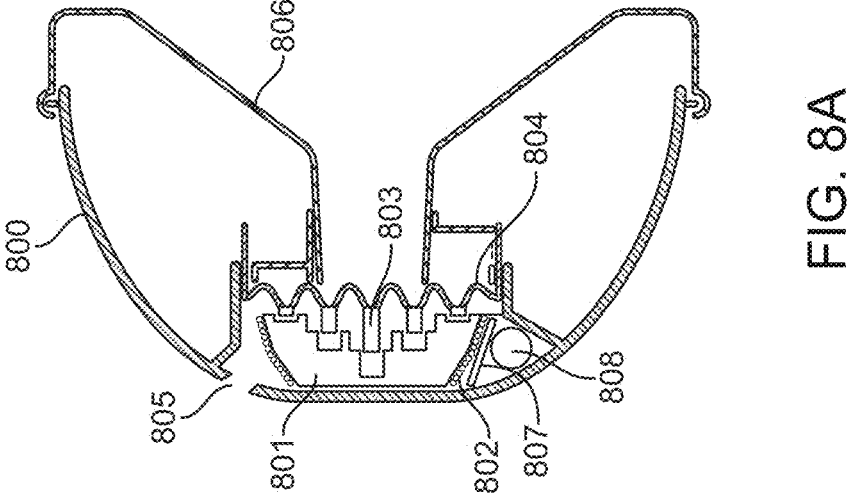

FIGS. 8A and 8B describe a wearable collection cup (800, 810) with an integrated breast pump. In FIG. 8A, the integrated breast pump consists of a solenoid coil (802), with a magnetic core (801) such as soft iron to concentrate the magnetic field, and the armature (803) also made of a magnetic core or magnet which is integrated into the diaphragm (804). When current is passed through the coil (802), a magnetic field is created which is concentrated into the soft iron core (801). This will attract the armature (803), thus pulling the diaphragm (804) in, creating a vacuum in the flange (806). The vent hole (805) is required to equalize the pressure when the solenoid is on. When current is turned off, the diaphragm (804) acts as the spring to return the armature (803) back to initial position, thus releasing the pressure within the flange (806) without the use of another solenoid as in a typical breast pump. The PCB (807) consisting of a control unit and the battery (808) will be used to control the breast pump, thus completing the integrated breast pump.

In FIG. 8A, the armature (803) does not need to be embedded into the diaphragm. It can be attached to a piston similar to (813).

In FIG. 8B, the integrated breast pump consists of a linear actuator, such as a voice coil actuator (moving magnet actuator or moving coil actuator). Other embodiments of the invention could replace a voice coil actuator with one or more of a voice coil and or piezo motor in various forms of series or parallel or with a voice coil or piezo motor drive system by themselves. FIG. 8B is an example of a moving coil actuator. The moving coil actuator consists of a yoke (811) made of magnetic core, with a permanent magnet (812) attached. The bobbin or coil holder (813) has a coil of wire (814) wound around, and the bobbin acts as a piston with rubber gasket (817) to ensure an air-tight seal. As current passes through the coil, a lateral force is created which drives the piston left and right. As the piston moves left and right, because of the air-tight seal, the diaphragm (815) also moves accordingly thus generating a vacuum on the flange (819). The vent hole (816) will equalize the pressure when the piston moves back and forth. A sensor (818) such as a hall-effect sensor or pressure sensor, can provide feedback resulting in the piston operating in a closed-feedback loop. This will allow for precise control of the vacuum created in the flange (819). The precise control of the piston movement will also allow for the breast pump to create micro-vibrations in the vacuum waveform to aid letdown. To release the vacuum in the flange (819) the current is reversed, causing the piston to move in the opposite direction thus releasing the vacuum in the flange (819). The PCB (820) consisting of a control unit and the battery (821) will be used to control the breast pump, thus completing the integrated breast pump. This design also does not require the use of an additional solenoid such as required in a traditional breast pump design.

In FIG. 8B, the bobbin does not need to be a separate assembly. The coil (814) can be embedded into the diaphragm (815) similar to (804).

Figure 9:
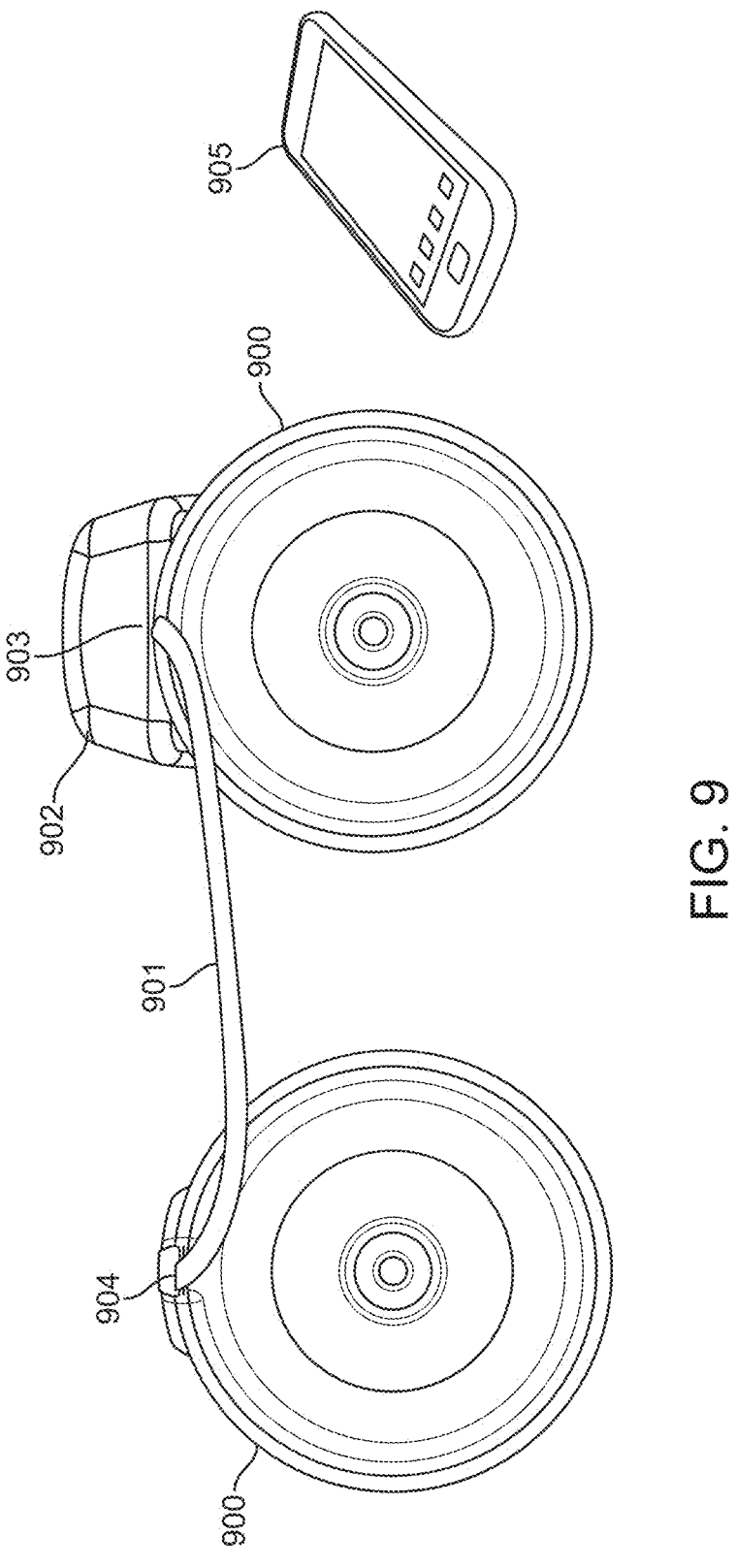
FIG. 9 is a front facing view of a wearable cup system for double pumping where a pump attaches to communicate suction to one collection cup by connecting directly and then connects indirectly to a second cup by using a connection tube to transmit suction to a second cup.

In FIG. 9 describes a system where two collection cups (900) can be used for double pumping, expression of milk from both breasts simultaneously or at a similar time concurrently or near concurrently. In this system one cup (900) or either cups (900) can be interchangeably or uniquely detached or attached to a source of suction such as an electromechanical vacuum pump (902) which comprises components such as a PCBA, vacuum motor, battery, and or other components such as buttons, Bluetooth antennas or other signaling systems, LCD or other display, or other mechanisms such as would be needed for a user to operate the system including a button or feature that enables the user to pump left side only, right side only, or both sides simultaneously with or without a time out feature such as a sleep timer. One vacuum pump system (902) is connected to one collection cup (900) almost directly through a connection in the base or side of the vacuum pump system (902) and it is connected to a second collection cup (900) through a connector tubing (901) that spans at least the distance between each of the cups if placed inside a brassier in operation. The connector tubing (901) connects the vacuum pump system (902) to the second cup (900) via a connector port on the second cup (904) that enables the suction from the vacuum pump system (902) to be transmitted through this connector tube (901) to the collection cup (900) in order to facilitate the expression of breastmilk or colostrum. The pump (902) could also be wirelessly, NFC, RF, or Bluetooth connected or other signal service connected such as but not limited to 3G or 4G to a mobile device or an additional remote control (905) such that the user could operate with or without buttons on the actual vacuum pump (902) but with or without a mobile or other separate operating control (905).

Figures 10A, 10B, 10C:
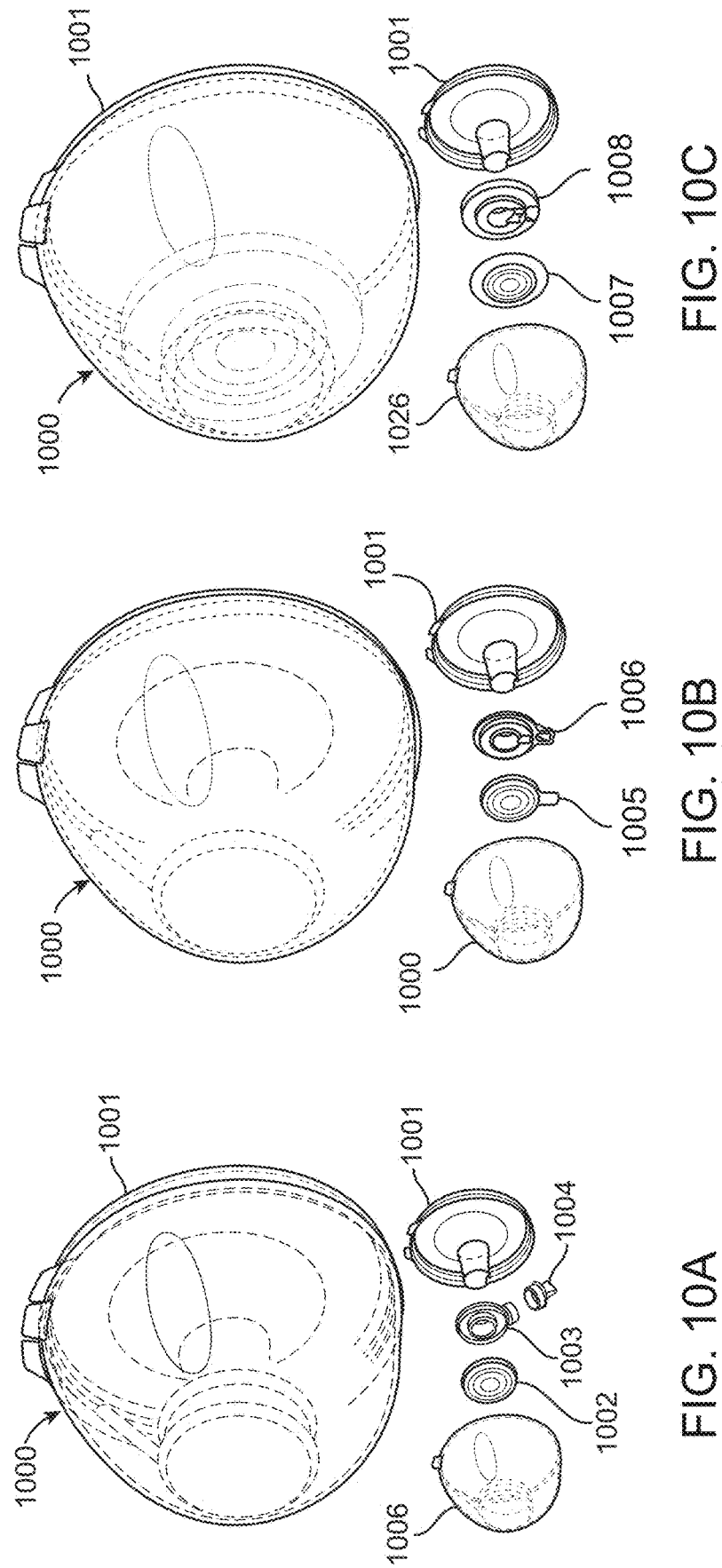
FIG. 10A-C are various views of collection cup design variations where the diaphragm and valve configurations vary.

In FIGS. 10A, B, and C, there are three exemplary embodiments of wearable collection cups that comprise a collection shell (1000) and a breast accepting cone (1001) that define a compartment for storage of milk and or colostrum expressed from the breast. In FIG. 10A the internal valve system comprises three parts including a cone accepting connector (1003) a duckbill valve (1004) and a pressure communicating diaphragm (1002). In FIG. 10B the internal valve system comprises two parts including an integrated pressure communicating diaphragm with a bill flap (1005) and a cone accepting connector (1006) with a milk flow channel. In FIG. 10C the internal valve system comprises two parts including an integrated pressure communicating diaphragm with uniform shape (1007) that eliminates orientation specific assembly and a cone accepting connector (1008) with a milk flow channel from the breast accepting compartment into the storage compartment.

Referring now to FIGS. 11-15, another system 1100 is shown, similar to the systems described above. Generally, the system 1100 is another compact, wearable breast pump with powerful, near-silent pumping. It has a large capacity bottle which can hold up to 8 fluid ounces of milk. The system 1100 has a nightlight feature to help see in the dark to set-up the pump and align the nipple.

The pump of the system 1100 is controlled via buttons on the device or a smart phone app. The smart phone app also provides feedback on how much milk is collected, pumping time, and/or suction level(s).

Figure 11:
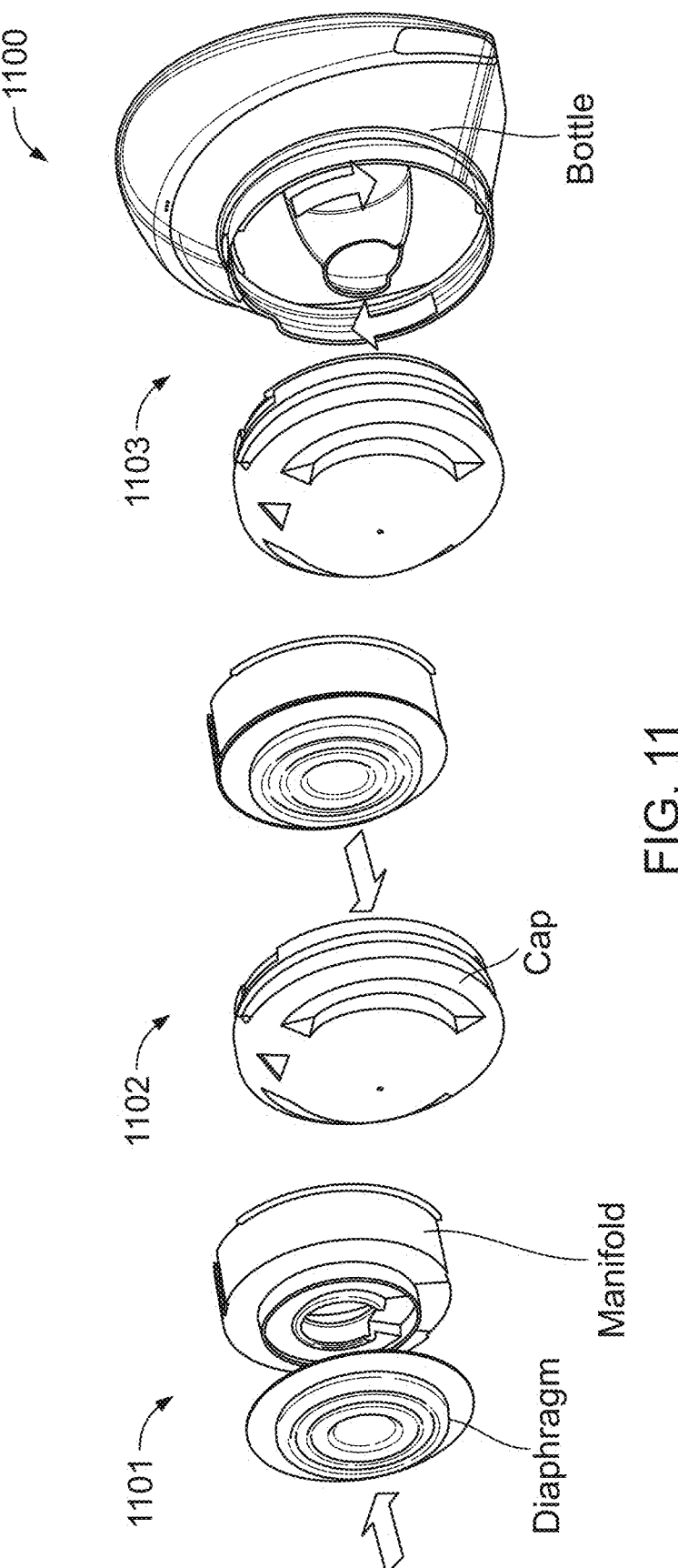
FIGS. 11-15 are various views of a collection cup system for a breastmilk collection device, according to one embodiment.

As shown in FIG. 11, before use, the milk collection bottle must be assembled, which is done in three steps. First, the diaphragm is pressed onto the manifold at 1101. Then, the manifold is pushed onto the cap at 1102. Finally, the cap is screwed onto the bottle (collection shell) at 1103.

Figure 12:
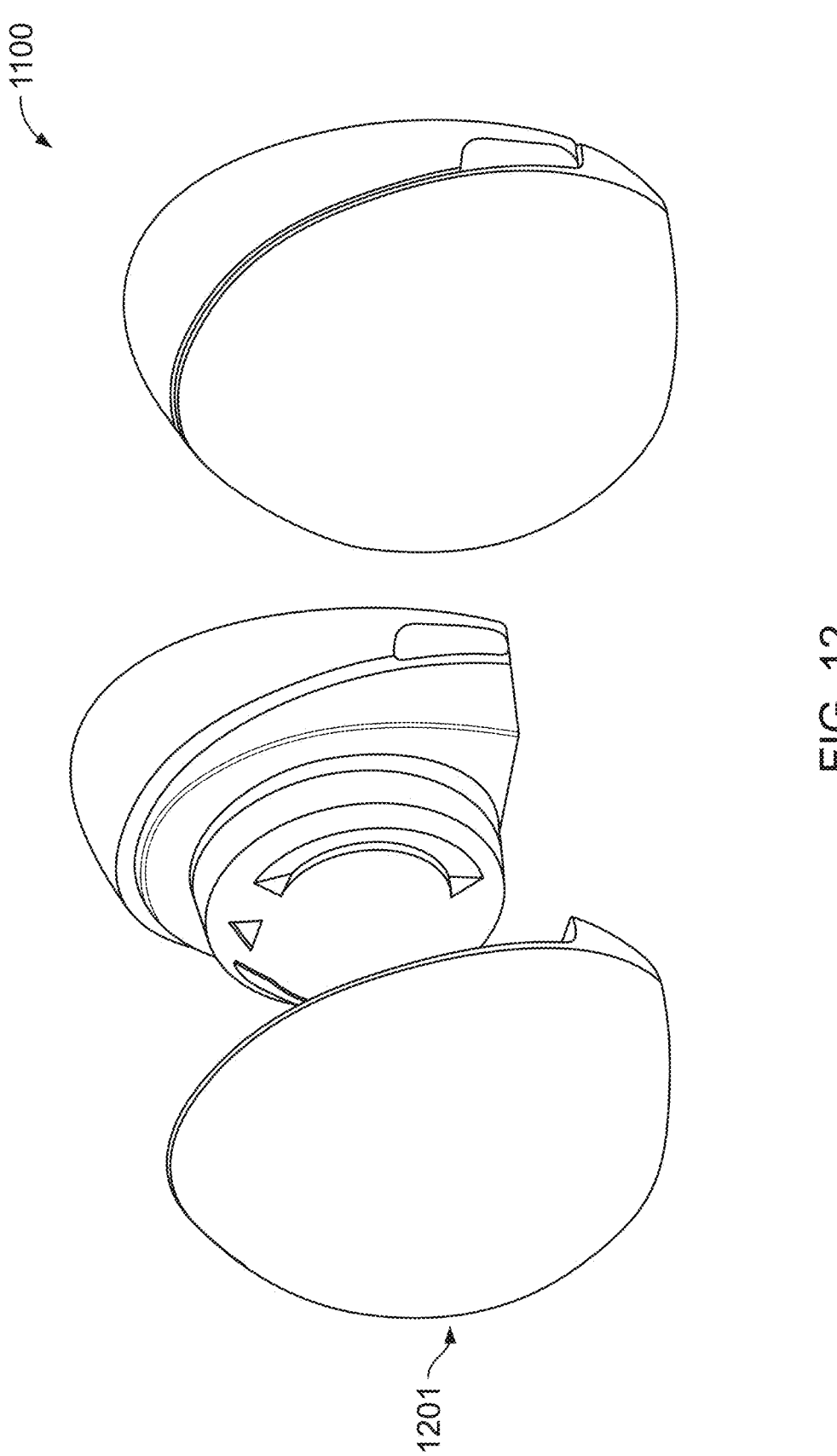

Next, in FIG. 12, the system 1100 is assembled. This is done by pushing the bottle into a pump 1201 until it clicks. The bottle is removed by pulling it away again.

Figure 13:
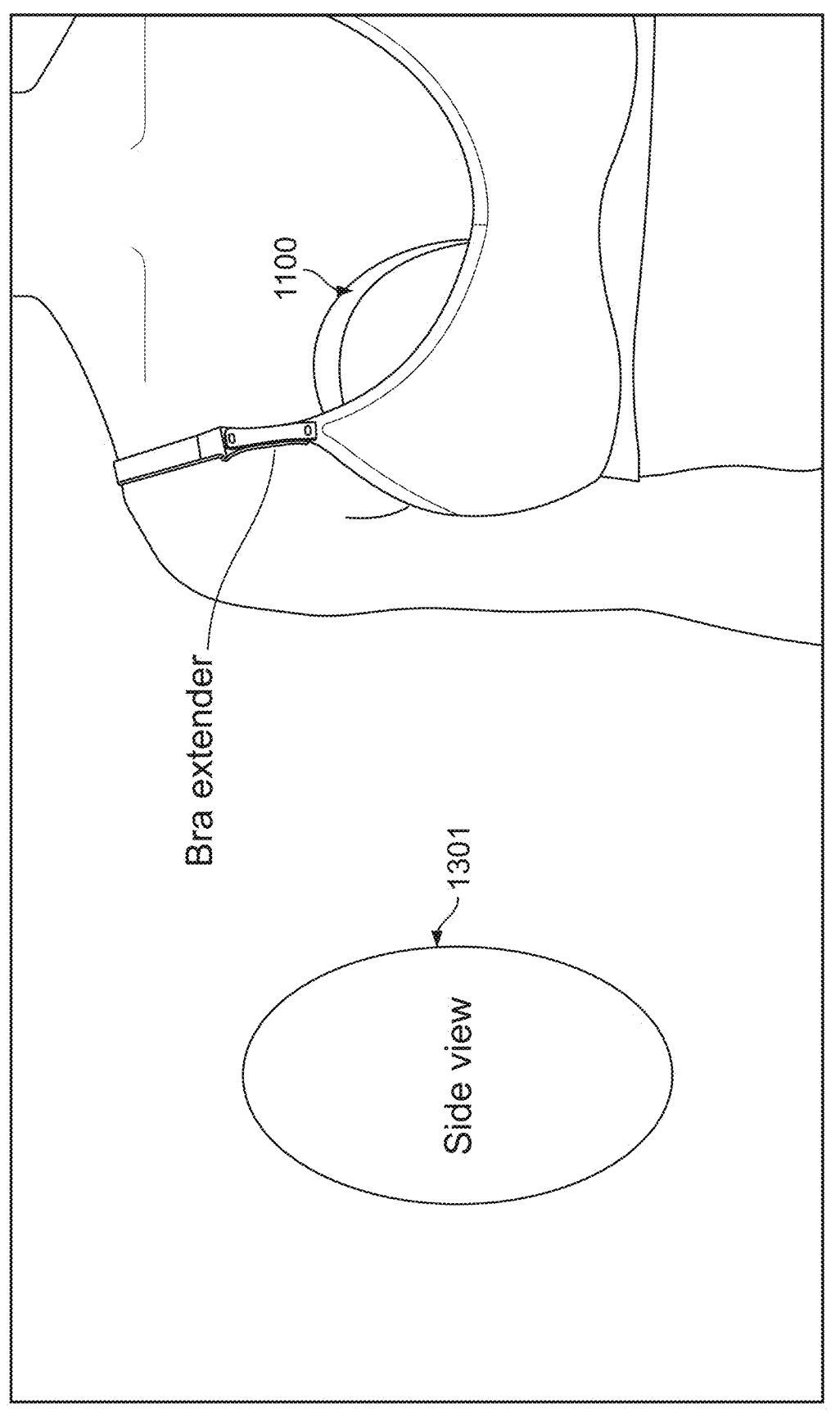

As shown in FIG. 13, the system 1100 including the pump is worn inside the bra and aligns to the nipple and breast. The system 1110 can include a bra extender 1301 enabling it to be worn with a standard nursing bra.

Figure 14:
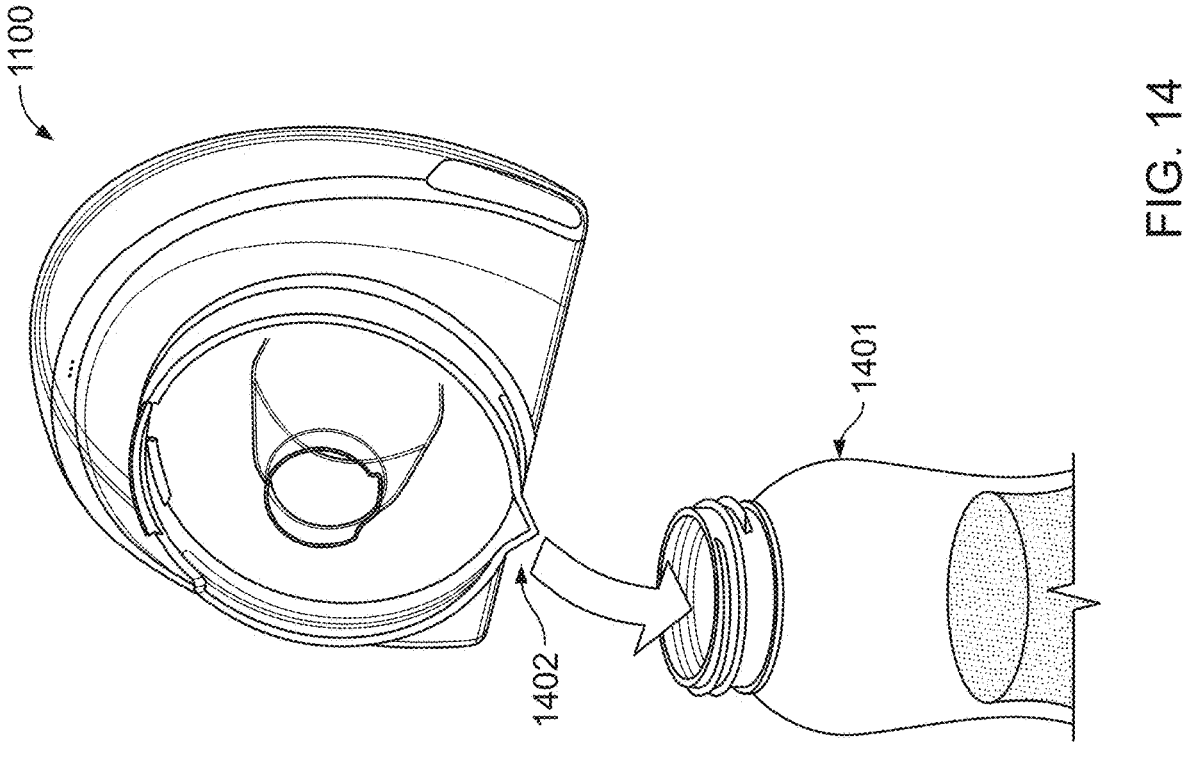

In FIG. 14, once the milk is collected in the bottle, the milk can be stored in the bottle. Alternatively, the cap can be removed, and the milk poured into a separate container 1401 using the integrated spout 1402.

Figure 15:
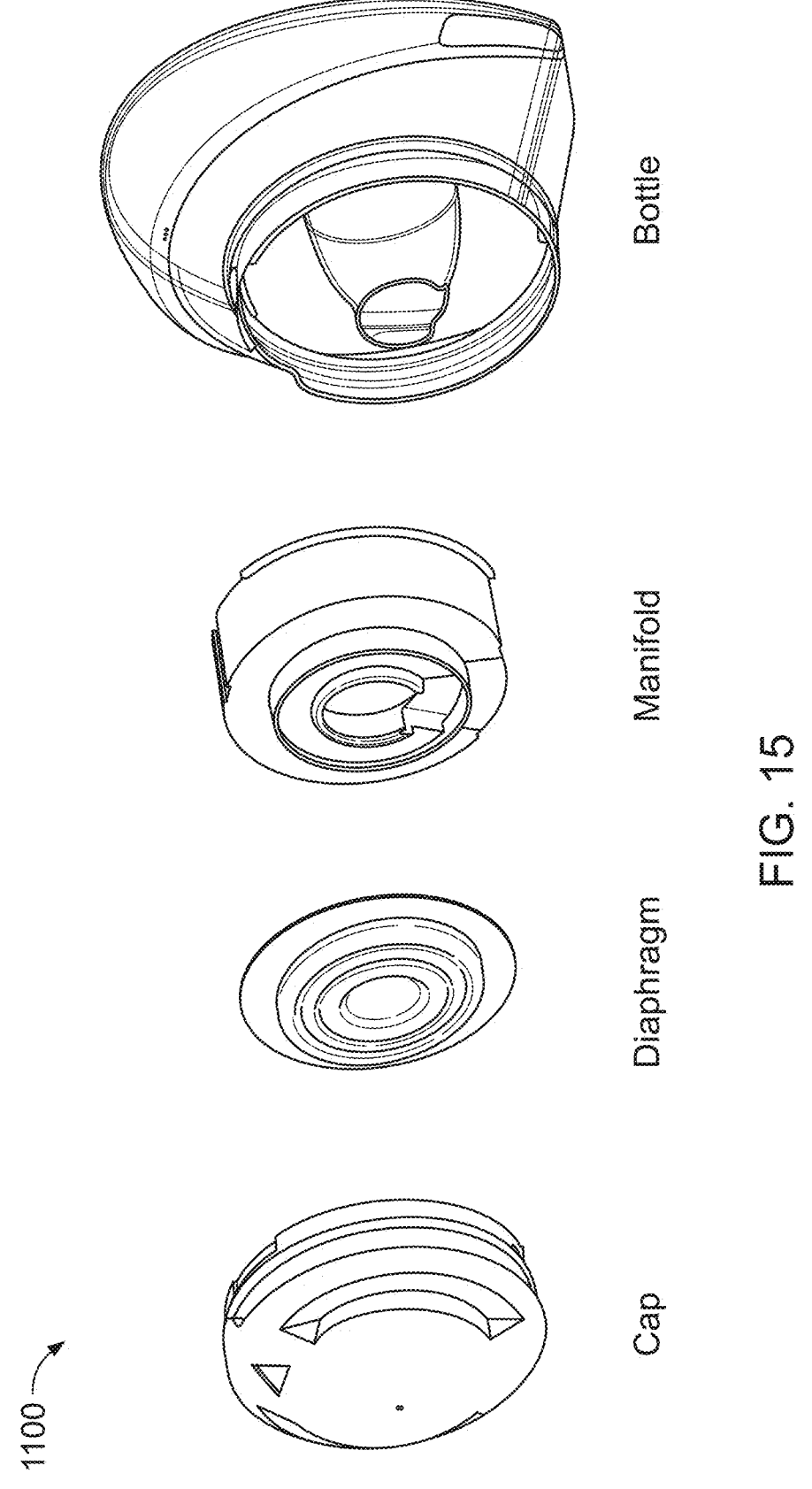

Finally, in FIG. 15, once the milk is decanted from the milk collection bottle, the system 1100 can be disassembled into its separate parts (cap, diaphragm, manifold, bottle) for cleaning. The parts can be washed by hand or in a dishwasher.

Referring now to FIGS. 16-19, another system 1600 is shown, similar to the systems described above. Generally, the system 1600 is another compact, wearable breast pump with powerful, near-silent pumping. It has a large capacity bottle which can hold up to 6 fluid ounces of milk. The system 1100 has a nightlight feature to help see in the dark to set-up the pump and align the nipple.

The pump of the system 1600 is controlled via buttons on the device, a remote control that may or may not include buttons to define which of multiple (two) pumps it is directing to operate in a specific function, or a smart phone app. The smart phone app also provides feedback on how much milk is collected, pumping time, and/or suction level(s).

Figure 16:
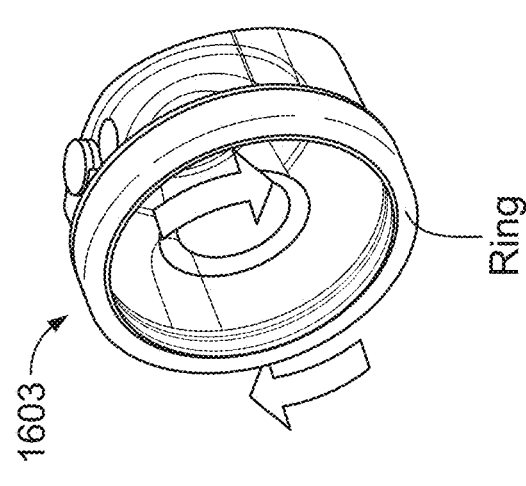
FIGS. 16-19 are various views of a collection cup system for a breastmilk collection device, according to one embodiment.
Figure 16:
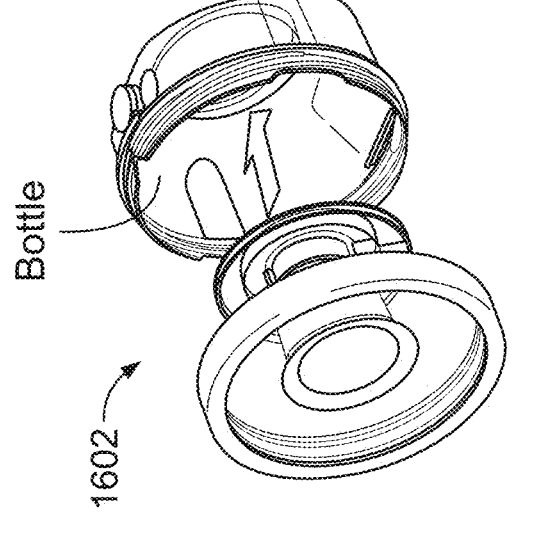
Figure 16:
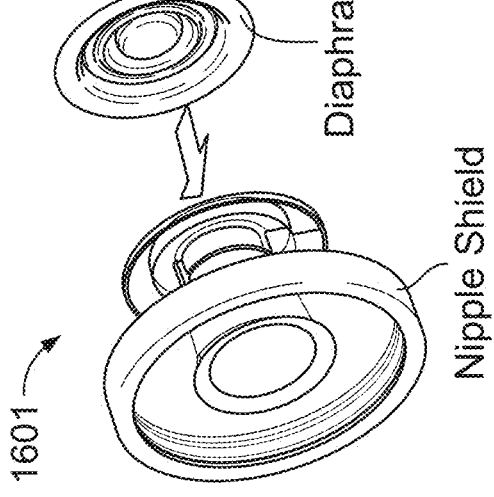

As shown in FIG. 16, before use, the milk collection bottle must be assembled, which is done in three steps. First, the diaphragm is pressed onto the nipple shield at 1601. Then, the nipple shield is pushed onto the bottle at 1602. Finally, a ring is rotated to lock the nipple shield into place in the bottle at 1603.

Figure 17:
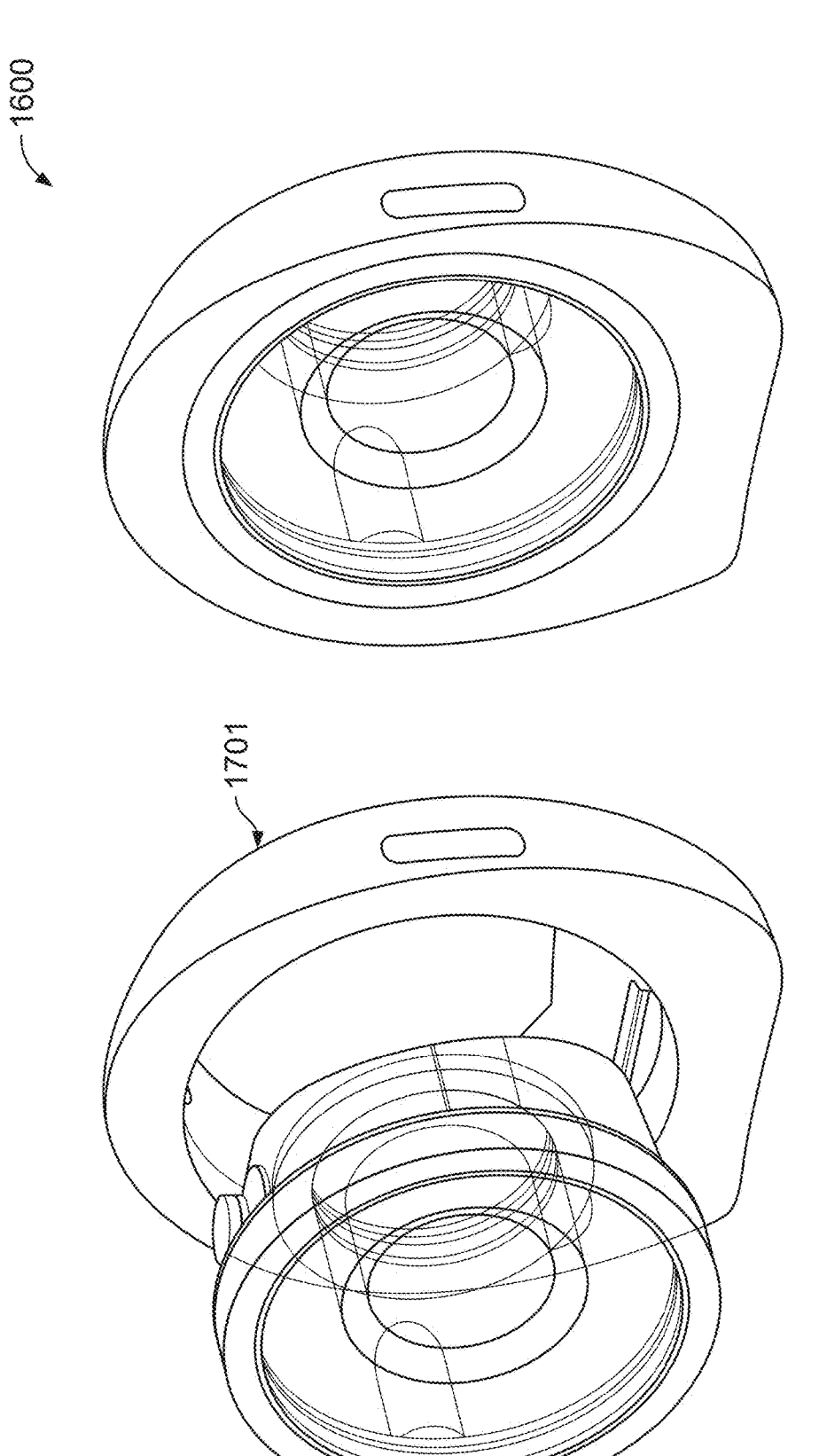

Next, in FIG. 17, the system 1600 is assembled. This is done by pushing the bottle into a pump 1701 until it clicks in place. The bottle is removed by squeezing the buttons on the side of the pump 1701.

The system 1600 including the pump is worn inside the bra and aligns to the nipple and breast. The system 1600 can include a bra extender 1301 enabling it to be worn with a standard nursing bra. See FIG. 13.

Figure 18:
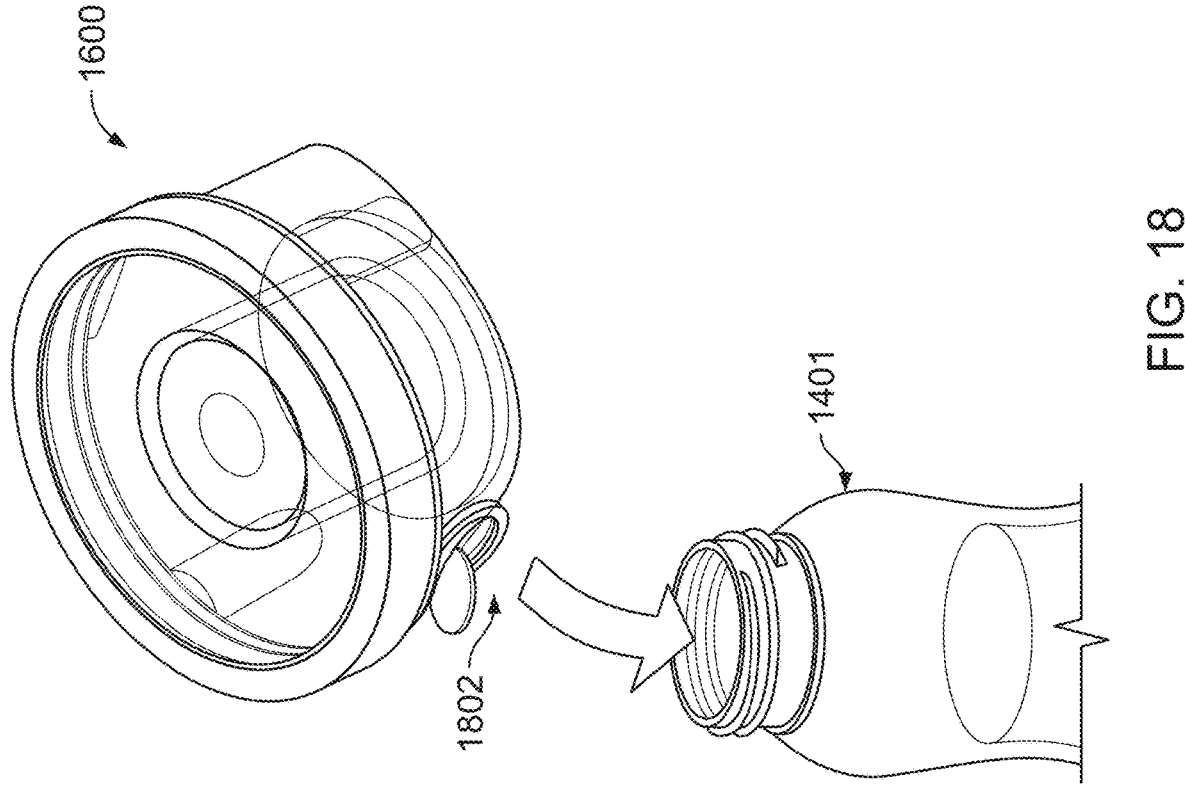

In FIG. 18, once the milk is collected in the bottle, the milk can be stored in the bottle. Alternatively, the cap can be removed, and the milk poured into the separate container 1401 by flipping open and using the integrated spout 1802.

Figure 19:
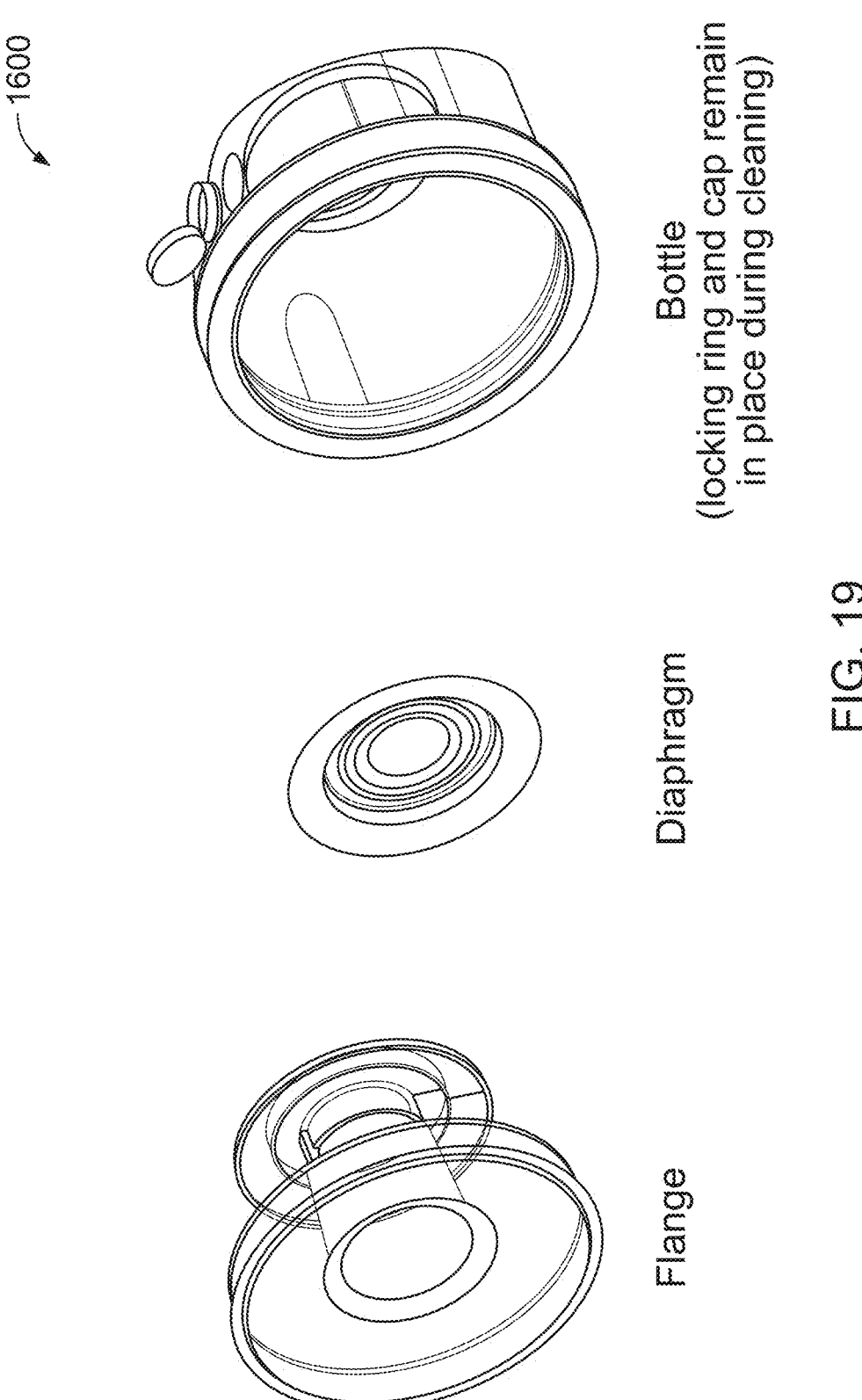

Finally, in FIG. 19, once the milk is decanted from the milk collection bottle, the system 1600 can be disassembled into its separate parts (flange, diaphragm, bottle-locking ring and cap remain in place) for cleaning. The parts can be washed by hand or in a dishwasher.

The components of the systems 1100, 1600 can be made of various materials for different looks and feels. In one option, the components are made of skin-colored, interchangeable shells. In another, the shells are covered with interchangeable fabric or other coverings that change the color, texture, and overall feel. In yet another embodiment, the shells are formed of various designs, with embellishments, such as metallic or other designs presented thereon.

Figures 20A, 20B, 20C:
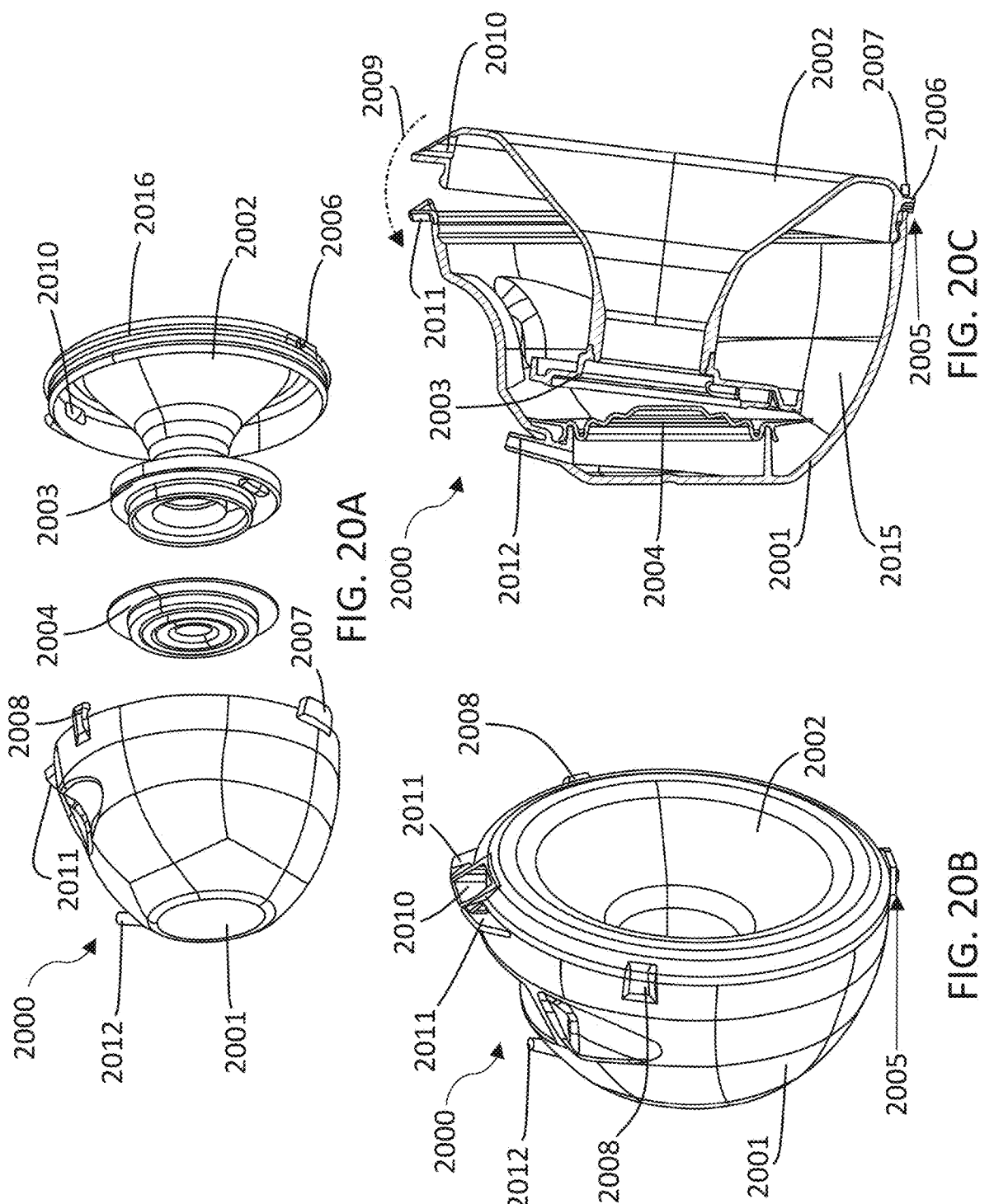
FIGS. 20A-C are various views of a collection cup system for a breastmilk collection device, according to one embodiment.
Figures 21A, 21B, 21C, 21D:
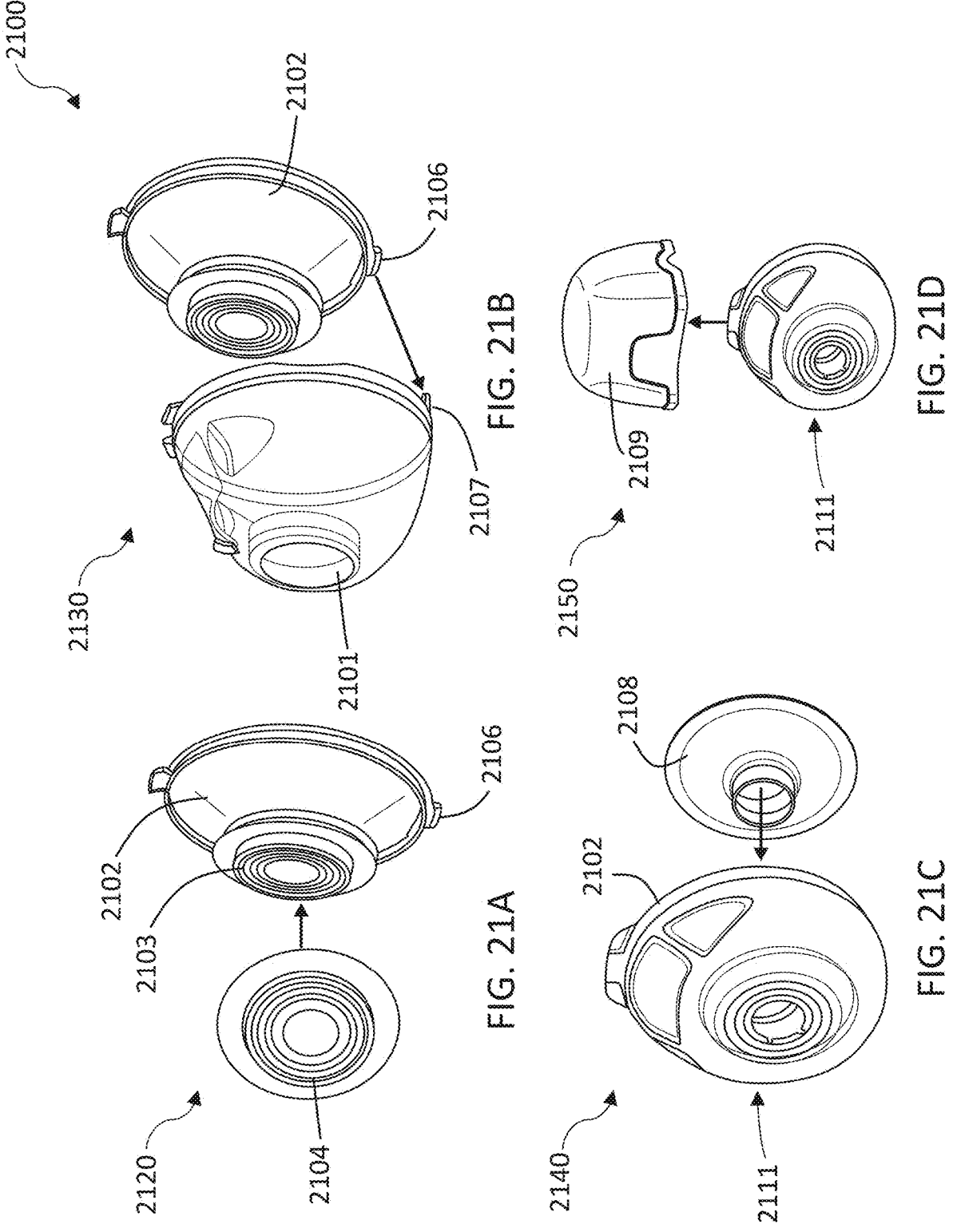
FIGS. 21A-D are various views of an assembly method of a collection cup system for a breastmilk collection device, according to one embodiment.

FIGS. 20A-C, illustrate another alternative embodiment of a wearable breastmilk collection cup (2000). The wearable breastmilk collection cup shares several similarities with breastmilk collection cups previously described, particularly the breastmilk collection cup described with reference to FIG. 4. The wearable collection cup (2000) includes a collection receptacle (2001), breast accepting flange chamber (2002), flange receiver (2003) and diaphragm/one-way valve (2004). The system contains a storage compartment (2015) that receives the expressed breastmilk and is contained within the collection receptacle (2001), breast accepting flange chamber (2002), and diaphragm/one-way valve (2004). The storage compartment (2015) is created by the coupling of the breast accepting flange chamber (2002) and the collection receptacle (2001) and is separated from the breast accepting flange chamber (2002) by the diaphragm/one-way valve (2004).

The breast accepting flange chamber (2002) and collection receptacle (2001) are attached to one another by a hinge assembly (2005) and at least one snap (2008). The hinge assembly (2005) is comprised of a hinge protrusion (2006) and a hinge receptacle (2007). The hinge protrusion (2006) and hinge receptacle (2007) are configured so that the hinge protrusion (2006) is received by the hinge receptacle (2007). As shown in FIGS. 20A-C, the hinge protrusion (2006) is defined by the breast accepting flange chamber (2002), and the hinge receptacle (2007) is defined by the collection receptacle (2001). However, in other implementations of the hinge assembly (2005), the hinge receptacle (2007) can be defined by the breast accepting flange chamber (2002) and the hinge protrusion (2006) can be defined by the collection receptacle (2001).

The wearable collection cup (2000) also comprises at least one snap (2008) to secure the collection receptacle (2001) and breast accepting flange chamber (2002) to one another. In an exemplary implementation, the collection receptacle (2001) defines two snaps (2008) that extend to engage and retain the breast accepting flange chamber (2002) such that the breast accepting flange chamber (2002) remains in contact with the collection receptacle (2001). This may be done, for example, by a raised geometry (2016) around the outer circumference of the breast accepting flange chamber (2002). During assembly, the snap(s) (2008) can be flexed to bend around the raised geometry (2016) and then return to an un-flexed position to retain the collection receptacle (2001) to the breast accepting flange chamber (2002). In an exemplary implementation, the collection receptacle (2001) defines two snaps (2008). In other implementations, the at least one snap (2008) can be defined by the breast accepting flange chamber (2002).

In an exemplary implementation, the wearable collection cup (2000) also comprises a flange chamber snap protrusion (2010) and collection receptacle snap protrusion (2011). As shown, the flange chamber snap protrusion (2010) is positioned on the breast accepting flange chamber (2002) and the collection receptacle snap protrusion (2011) is positioned on the collection receptacle (2011). However, it is to be appreciated that in other implementations, the flange chamber snap protrusion (2010) could be defined by the collection receptacle (2001) and the collection receptacle snap protrusion (2011) could be defined by the breast accepting flange chamber (2002). The collection receptacle snap protrusion (2011) defines a gap in which the flange chamber snap protrusion (2010) is received. Like the snap (2008), the collection receptacle snap protrusion (2011) and flange chamber snap protrusion (2010) can retain one another by flexing, a friction fit, or other retention mechanisms. As another exemplary advantage of the collection receptacle snap protrusion (2011) and flange chamber snap protrusion (2010), a user can open the wearable collection cup (2000) by pulling or pushing on the flange chamber snap protrusion (2010) through the opening defined by the collection receptacle snap protrusion (2011).

An exemplary advantage of the hinge assembly (2005) of the wearable collection cup (2000) is the reduction of potential user error during assembly. To attach the collection receptacle (2001) and breast accepting flange chamber (2002) to one another, a user must first insert the hinge protrusion (2006) into the hinge receptacle (2007). Once inserted, a user can close the wearable collection cup (2000) by pivoting the collection receptacle (2001) and breast accepting flange chamber (2002) around the hinge assembly (2005), as indicated by the pivot direction arrow (2009). By using the hinge assembly (2005), misalignment is prevented during assembly, which ensures a proper seal and prevents breastmilk from leaking from a storage compartment (2015).

Referring now to FIGS. 21A-D, an assembly method of a collection cup (2100) system for a breastmilk collection device is shown, according to one embodiment. The method comprises a first step (2120) of placing a diaphragm (2104) on to a flange receiver (2103) of a breast accepting flange chamber (2102). In an exemplary first step (2120), the diaphragm (2104) is positioned on the flange receiver (2103) such that there are no gaps or spaces between the diaphragm (2104) and flange receiver (2103).

The method also comprises a second step (2130) of inserting a hinge protrusion (2106) into a hinge receptacle (2107) and pivoting a collection receptacle (2101) and/or the breast accepting flange chamber (2102) to close them together. In an exemplary second step (2130), snaps retain the collection receptacle (2101) and breast accepting flange chamber (2102) to one another such that there are no gaps or spaces between the collection receptacle (2101) and breast accepting flange chamber (2102).

The method also comprises an optional third step (2140) of inserting a silicon insert (2108) into the breast accepting flange chamber (2102). In an exemplary implementation, the silicon insert (2108) comprises a 21 mm, 25 mm, or 28 mm silicon insert (2108) and is tightly inserted such that there are no gaps between the silicon insert (2108) and breast accepting flange chamber (2102) and there is no loss of suction.

The method also comprises an optional fourth step (2150) of attaching a pump hub (2109) by inserting a pour spout of the breastmilk collection cup (2111) into a notch located at the bottom of the pump hub (2109).

Figures 22A, 22B, 22C, 22D:
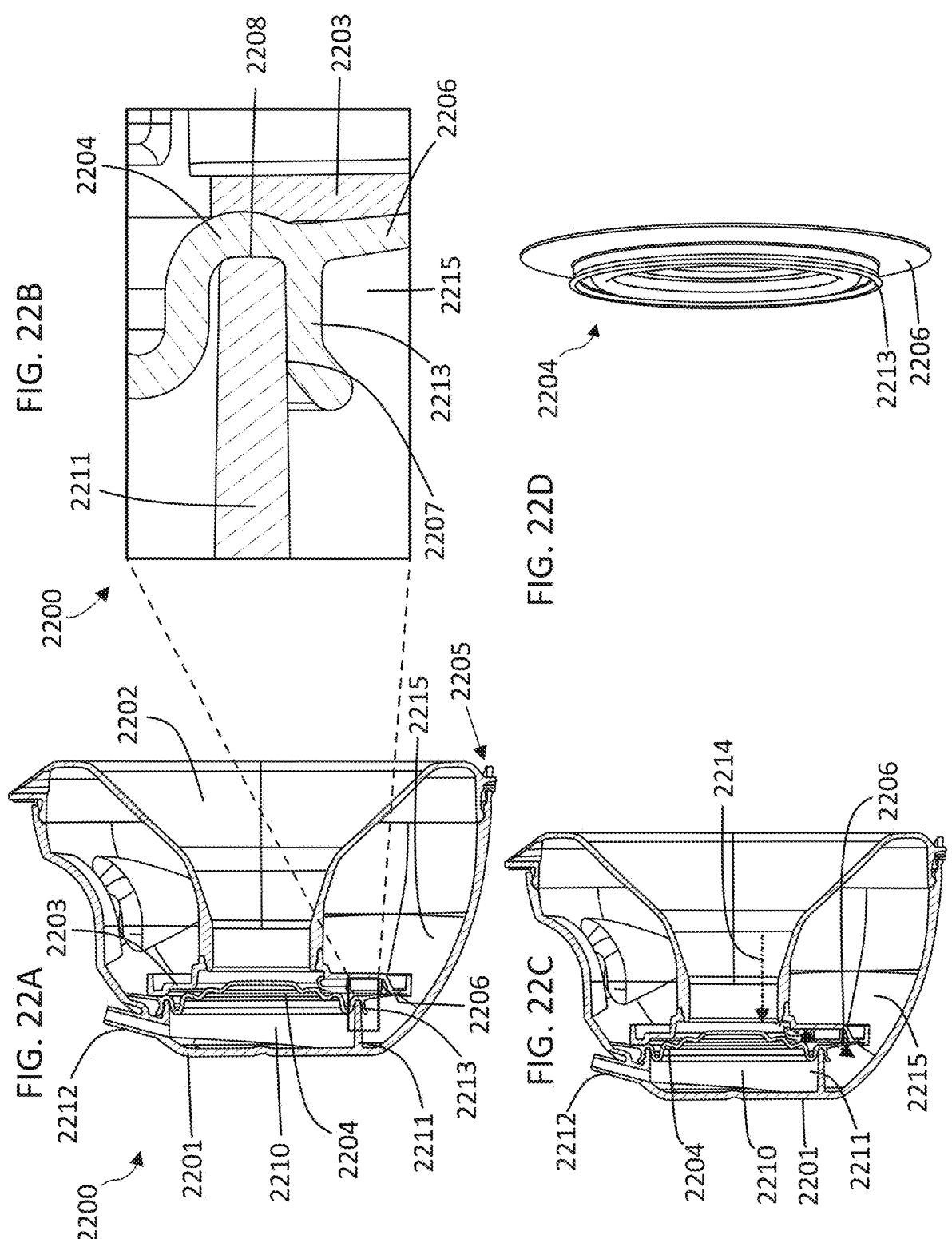
FIGS. 22A-C are various views of a collection cup system for a breastmilk collection device, according to one embodiment.
FIG. 22D is a side perspective view of a diaphragm/one-way valve, according to one embodiment.

Referring now to FIGS. 22A-C, various views of a collection cup system for a breastmilk collection device (2200) are shown, according to an exemplary embodiment. The wearable collection cup (2200) is substantially similar to those collection cups previously described, particularly with reference to the collection cup of FIGS. 4A-D. The collection cup (2200) includes a collection receptacle (2201), breast accepting flange chamber (2202), flange receiver (2203), and diaphragm/one-way valve (2204). The storage compartment (2215) is created by the coupling of the breast accepting flange chamber (2202) and the collection receptacle (2201) and is separated from a breast accepting flange chamber (2202) by the diaphragm/one-way (2204). The diaphragm/one-way valve (2204) further separates an isolated reservoir (2210) from both the breast accepting flange chamber (2202) and storage compartment (2215). The isolated reservoir (2210) is thus shaped and sealed by the collection receptacle (2201), an isolated reservoir cylinder (2211) that extends into the collection receptacle (2201), and the diaphragm/one-way valve (2204), which is pressed between the isolated reservoir cylinder (2211) and flange receiver (2203). The isolated reservoir (2210) is in fluid communication with an external vacuum source attachment port (2012), which is configured to provide a low pressure to the isolated reservoir (2210) relative to the breast accepting flange chamber (2202).

As best seen in FIGS. 22B & 22D, the diaphragm/one-way valve (2204) includes a lip (2213). The lip (2213) is configured to wrap around the isolated reservoir cylinder (2211) such that the lip (2213) is exposed to the storage compartment (2215) and not the isolated reservoir (2210). In this manner, the lip (2213) creates an outer seal (2207) between the storage compartment (2215) and isolated reservoir (2210). Also, as previously mentioned, the diaphragm/one-way valve (2204) is pressed between the isolated reservoir cylinder (2211) and the flange receiver (2203), creating an inner seal (2208). An exemplary benefit of having both the outer seal (2207) and inner seal (2208) is that even if the collection receptacle (2201) and breast accepting flange chamber (2202) are not perfectly aligned during assembly, the outer seal (2207) formed by the lip (2213) and the isolated reservoir cylinder (2211) prevents leakage from the storage compartment (2215) into the isolated reservoir (2210).

The diaphragm/one-way valve (2204) includes an integrated one-way valve (2206) shown as but not limited to a flapper valve. As low pressure is applied to the isolated reservoir (2210), the diaphragm (2204) flexes and communicates the vacuum force from the isolated reservoir (2210) to the breast accepting flange chamber (2202) to extract milk from the breast. The extracted milk is then able to move along the flow path illustrated by arrows (2214), past the one-way valve (2206) and into the storage compartment (2215).

Many other configurations are possible.

The invention claimed is:

1. A wearable breastmilk collection device comprising:
   a collection receptacle;
   a flange chamber, wherein the flange chamber and the collection receptacle comprise a hinge assembly configured to pivot the flange chamber and the collection receptacle to a closed position to form a storage compartment for receiving breastmilk defined by the flange chamber and the collection receptacle;
   at least one snap configured to secure the flange chamber and the collection receptacle together in the closed position; and
   a diaphragm disposed between the flange chamber and the collection receptacle wherein in the closed position the diaphragm acts as a one-way valve between the flange chamber and the storage compartment.

2. The wearable breastmilk collection device of claim 1, wherein the hinge assembly comprises a hinge protrusion and a hinge receptacle, wherein the hinge protrusion is configured to be received by the hinge receptacle.

3. The wearable breastmilk collection device of claim 2, wherein the hinge protrusion is defined by the flange chamber and the hinge receptacle is defined by the collection receptacle.

4. The wearable breastmilk collection device of claim 1, wherein the at least one snap comprises two snaps defined by the collection receptacle that extend to engage and retain the flange chamber.

5. The wearable breastmilk collection device of claim 4, wherein the flange chamber defines a raised geometry around an outer circumference, and wherein the two snaps are configured to flex around the raised geometry and return to an un-flexed position to retain the collection receptacle to the flange chamber.

6. The wearable breastmilk collection device of claim 1, further comprising a flange chamber snap protrusion positioned on the flange chamber and a collection receptacle snap protrusion positioned on the collection receptacle, wherein the collection receptacle snap protrusion defines a gap in which the flange chamber snap protrusion is received.

7. The wearable breastmilk collection device of claim 1, further comprising an isolated reservoir formed between the collection receptacle and the diaphragm, wherein the isolated reservoir is configured to receive vacuum pressure from an external vacuum source.

8. A method of assembling a breastmilk collection device, the method comprising:

placing a diaphragm on a flange receiver of a flange chamber;

inserting a hinge protrusion into a hinge receptacle;

pivoting the flange chamber and a collection receptacle around the hinge protrusion and the hinge receptacle to a closed position to form a storage compartment for receiving breastmilk defined by the flange chamber and the collection receptacle; and engaging at least one snap to retain the flange chamber and the collection receptacle in the closed position wherein in the closed position the diaphragm acts as a one-way valve between the flange chamber and the storage compartment.

9. The method of claim 8, wherein the hinge protrusion is defined by the flange chamber and the hinge receptacle is defined by the collection receptacle.

10. The method of claim 8, wherein engaging the at least one snap comprises flexing two snaps defined by the collection receptacle around a raised geometry of the flange chamber.

11. The method of claim 8, further comprising inserting a silicon insert into the flange chamber after engaging the at least one snap.

12. The method of claim 11, wherein the silicon insert is inserted such that there are no gaps between the silicon insert and the flange chamber.

13. The method of claim 8, further comprising attaching a pump hub by inserting a pour spout of the breastmilk collection device into a notch located at a bottom of the pump hub.

* * * * *